(12) United States Patent
Schilling et al.

(10) Patent No.: US 11,923,079 B1
(45) Date of Patent: *Mar. 5, 2024

(54) CREATING AND TESTING DIGITAL BIO-MARKERS BASED ON GENETIC AND PHENOTYPIC DATA FOR THERAPEUTIC INTERVENTIONS AND CLINICAL TRIALS

(71) Applicant: Vignet Incorporated, Fairfax, VA (US)

(72) Inventors: Josh Schilling, Salem, OR (US); Praduman Jain, Fairfax, VA (US)

(73) Assignee: VigNet Incorporated, Fairfax, VA (US)

( * ) Notice: Subject to any disclaimer, the term of this patent is extended or adjusted under 35 U.S.C. 154(b) by 284 days.

This patent is subject to a terminal disclaimer.

(21) Appl. No.: 17/381,951

(22) Filed: Jul. 21, 2021

Related U.S. Application Data

(63) Continuation of application No. 16/266,516, filed on Feb. 4, 2019, now Pat. No. 11,238,979, which is a
(Continued)

(51) Int. Cl.
  *G16H 40/40* (2018.01)
  *G06N 20/00* (2019.01)
  (Continued)

(52) U.S. Cl.
  CPC ............ *G16H 10/40* (2018.01); *G06N 20/00* (2019.01); *G06Q 10/063* (2013.01); *G16H 15/00* (2018.01); *G16H 20/10* (2018.01)

(58) Field of Classification Search
  CPC ........ G16H 40/40; G16H 15/00; G16H 20/10; G06N 20/00; G06Q 10/063
  See application file for complete search history.

(56) References Cited

U.S. PATENT DOCUMENTS 6,019,777 A    2/2000  Mackenzie
6,039,688 A    3/2000  Douglas et al.
(Continued)

FOREIGN PATENT DOCUMENTS

EP         2545468        1/2016
WO    WO 2011112556       9/2011
(Continued)

OTHER PUBLICATIONS

[No Author Listed] "Cancer Care Patient Navigation. A practical guide for community cancer centers," Association of Community Cancer Centers, 2009, [retrieved on Jan. 2, 2018], retrieved from: URL <https://www.accc-cancer.org/resources/pdf/Patient-Navigation-Guide.pdf>, 40 pages.
(Continued)

*Primary Examiner* — Michael I Ezewoko
(74) *Attorney, Agent, or Firm* — Fish & Richardson P.C.

(57) ABSTRACT

Systems and methods for inferring medication adherence levels using markers and predictive models are described. In some implementations, a system evaluates a degree to which a set physiological parameters is predictive of whether a subject has taken a medication. The system stores a predictive marker for inferring medication adherence. The system selects a subject that is designated to take the medication, causes one or more devices associated with the selected subject to change data collection parameters to measure values for the set of physiological parameters, and determines whether the selected subject took the medication based on the predictive marker and the data collected from the one or devices.

20 Claims, 13 Drawing Sheets

Related U.S. Application Data continuation of application No. 16/264,769, filed on Feb. 1, 2019, now Pat. No. 10,762,990.

(51) Int. Cl.
  *G06Q 10/063*  (2023.01)
  *G16H 10/40*  (2018.01)
  *G16H 15/00*  (2018.01)
  *G16H 20/10*  (2018.01)

(56) References Cited

U.S. PATENT DOCUMENTS

| | | |
|---|---|---|
| 6,260,022 B1 | 7/2001 | Brown |
| 6,269,339 B1 | 7/2001 | Silver |
| 6,828,992 B1 | 12/2004 | Freeman |
| 6,904,408 B1 | 6/2005 | McCarthy |
| 7,076,534 B1 | 7/2006 | Cleron et al. |
| 7,086,007 B1 | 8/2006 | Bushey |
| 7,330,717 B2 | 2/2008 | Gidron et al. |
| 7,433,853 B2* | 10/2008 | Brockway ............ A61B 5/7475 706/45 |
| 7,447,643 B1 | 11/2008 | Olson et al. |
| 7,730,063 B2 | 6/2010 | Eder |
| 7,953,613 B2 | 5/2011 | Gizewski |
| 8,347,263 B1 | 1/2013 | Offer |
| 8,997,038 B2 | 3/2015 | Becker |
| 9,134,964 B2 | 9/2015 | Hirsch |
| 9,170,800 B2 | 10/2015 | Lang |
| 9,361,011 B1 | 6/2016 | Burns |
| 9,426,433 B1 | 8/2016 | Mazzarella |
| 9,461,972 B1 | 10/2016 | Mehta |
| 9,715,370 B2 | 7/2017 | Friedman |
| 9,753,618 B1 | 9/2017 | Jain |
| 9,844,725 B1 | 12/2017 | Durkin et al. |
| 9,848,061 B1 | 12/2017 | Jain et al. |
| 9,858,063 B2 | 1/2018 | Jain et al. |
| 9,983,775 B2 | 5/2018 | Jain et al. |
| 10,039,451 B2* | 8/2018 | Gross ................. A61B 5/0002 |
| 10,095,838 B2* | 10/2018 | Hebler .................. G16Z 99/00 |
| 10,202,769 B2 | 2/2019 | Gya |
| 10,205,769 B2 | 2/2019 | Sehgal |
| 10,482,135 B2 | 11/2019 | Rychikhin |
| 10,521,557 B2 | 12/2019 | Jain |
| 10,705,816 B2 | 7/2020 | Jain et al. |
| 10,762,990 B1 | 9/2020 | Schilling et al. |
| 10,775,974 B2 | 9/2020 | Schilling et al. |
| 2001/0019338 A1 | 9/2001 | Roth |
| 2002/0010596 A1 | 1/2002 | Matory |
| 2002/0022973 A1 | 2/2002 | Sun |
| 2002/0157091 A1 | 10/2002 | DeMello et al. |
| 2003/0078960 A1 | 4/2003 | Murren et al. |
| 2003/0165954 A1 | 9/2003 | Katagiri et al. |
| 2003/0182429 A1 | 9/2003 | Jagels |
| 2003/0229522 A1 | 12/2003 | Thompson et al. |
| 2004/0030424 A1 | 2/2004 | Corl |
| 2004/0203755 A1 | 10/2004 | Brunet et al. |
| 2004/0216054 A1 | 10/2004 | Matthews |
| 2005/0050320 A1 | 3/2005 | Wassmann et al. |
| 2005/0055687 A1 | 3/2005 | Mayer |
| 2005/0086587 A1 | 4/2005 | Balz |
| 2005/0144072 A1 | 6/2005 | Perkowski et al. |
| 2005/0186550 A1 | 8/2005 | Gillani |
| 2005/0246304 A1 | 11/2005 | Knight et al. |
| 2006/0010090 A1* | 1/2006 | Brockway ............ A61B 5/7475 600/300 |
| 2006/0041452 A1 | 2/2006 | Kukarni |
| 2006/0107219 A1 | 5/2006 | Ahya |
| 2006/0205564 A1 | 9/2006 | Peterson |
| 2006/0241972 A1* | 10/2006 | Lang ..................... G16H 10/60 705/2 |
| 2006/0282516 A1 | 12/2006 | Taylor |
| 2007/0021984 A1 | 1/2007 | Brown |
| 2007/0118054 A1* | 5/2007 | Pinhas ................. G16H 40/67 600/587 |
| 2007/0172844 A1 | 7/2007 | Lancaster et al. |
| 2007/0231828 A1 | 10/2007 | Beachy et al. |
| 2007/0259351 A1 | 11/2007 | Chinitz et al. |
| 2007/0281285 A1 | 12/2007 | Jayaweera |
| 2008/0005679 A1 | 1/2008 | Rimas-Ribikauskas |
| 2008/0021287 A1* | 1/2008 | Woellenstein ......... G16H 50/30 600/300 |
| 2008/0034314 A1 | 2/2008 | Louch et al. |
| 2008/0046038 A1 | 2/2008 | Hill et al. |
| 2008/0126110 A1 | 5/2008 | Haeberle |
| 2008/0127040 A1 | 5/2008 | Barcellona |
| 2008/0177638 A1 | 7/2008 | Butler |
| 2008/0201174 A1 | 8/2008 | Ramsubramanian |
| 2008/0214904 A1* | 9/2008 | Saeed .................... G16H 40/63 705/2 |
| 2008/0242221 A1 | 10/2008 | Shapiro et al. |
| 2008/0243038 A1 | 10/2008 | Bennett |
| 2008/0254429 A1 | 10/2008 | Woolf et al. |
| 2008/0261191 A1 | 10/2008 | Woolf et al. |
| 2008/0301118 A1 | 12/2008 | Chien |
| 2008/0311968 A1 | 12/2008 | Hunter |
| 2009/0023555 A1 | 1/2009 | Raymond |
| 2009/0024944 A1 | 1/2009 | Louch |
| 2009/0031215 A1 | 1/2009 | Collier |
| 2009/0035733 A1 | 2/2009 | Meitar |
| 2009/0043689 A1 | 2/2009 | Yang |
| 2009/0076856 A1 | 3/2009 | Darby et al. |
| 2009/0119678 A1 | 5/2009 | Shih |
| 2009/0125333 A1 | 5/2009 | Heywood |
| 2009/0150814 A1 | 6/2009 | Eyer |
| 2009/0156190 A1 | 6/2009 | Fisher |
| 2009/0163182 A1 | 6/2009 | Gatti |
| 2009/0170715 A1 | 7/2009 | Glinsky |
| 2009/0172002 A1 | 7/2009 | Bathiche |
| 2009/0248883 A1 | 10/2009 | Suryanarayana et al. |
| 2009/0276771 A1 | 11/2009 | Nickolov et al. |
| 2010/0041378 A1 | 2/2010 | Aceves |
| 2010/0063367 A1 | 3/2010 | Friedman et al. |
| 2010/0082367 A1 | 4/2010 | Hains et al. |
| 2010/0106524 A1* | 4/2010 | Wu .......................... G06Q 40/08 705/3 |
| 2010/0122286 A1 | 5/2010 | Begeja |
| 2010/0179833 A1 | 7/2010 | Roizen et al. |
| 2010/0211941 A1 | 8/2010 | Roseborough |
| 2010/0250341 A1 | 9/2010 | Hauser |
| 2010/0262664 A1 | 10/2010 | Brown et al. |
| 2010/0333037 A1 | 12/2010 | Pavlovski |
| 2011/0077971 A1 | 3/2011 | Surwit et al. |
| 2011/0126119 A1 | 5/2011 | Young |
| 2011/0184748 A1 | 7/2011 | Fierro et al. |
| 2011/0200979 A1 | 8/2011 | Benson |
| 2011/0230360 A1 | 9/2011 | Stephan et al. |
| 2012/0047029 A1 | 2/2012 | Veres et al. |
| 2012/0065987 A1 | 3/2012 | Farooq et al. |
| 2012/0084399 A1 | 4/2012 | Scharber et al. |
| 2012/0102050 A1 | 4/2012 | Button |
| 2012/0143697 A1 | 6/2012 | Chopra |
| 2012/0157793 A1 | 6/2012 | MacDonald |
| 2012/0215639 A1 | 8/2012 | Ramer et al. |
| 2012/0220835 A1 | 8/2012 | Chung |
| 2012/0260294 A1 | 10/2012 | Reichardt et al. |
| 2012/0272156 A1 | 10/2012 | Kerger |
| 2013/0006064 A1 | 1/2013 | Reiner |
| 2013/0103749 A1 | 4/2013 | Werth et al. |
| 2013/0110565 A1 | 5/2013 | Means |
| 2013/0145457 A1 | 6/2013 | Papkipos et al. |
| 2013/0166494 A1 | 6/2013 | Davis |
| 2013/0179472 A1 | 7/2013 | Junqua |
| 2013/0185097 A1 | 7/2013 | Saria et al. |
| 2013/0212487 A1 | 8/2013 | Cote |
| 2013/0238686 A1 | 9/2013 | O'Donoghue |
| 2013/0283188 A1 | 10/2013 | Sanghvi |
| 2013/0329632 A1 | 12/2013 | Buyukkoc et al. |
| 2014/0019191 A1 | 1/2014 | Mulji |
| 2014/0019480 A1 | 1/2014 | Rychikhin |
| 2014/0026113 A1 | 1/2014 | Farooqi |
| 2014/0033171 A1 | 1/2014 | Lorenz |
| 2014/0052681 A1 | 2/2014 | Nitz et al. |
| 2014/0058755 A1 | 2/2014 | Macoviak et al. |

(56) References Cited

U.S. PATENT DOCUMENTS

| | | | |
|---|---|---|---|
| 2014/0081092 A1* | 3/2014 | McNair | G16H 40/20 600/301 |
| 2014/0087961 A1 | 3/2014 | Sulem et al. | |
| 2014/0088995 A1 | 3/2014 | Damani | |
| 2014/0100883 A1 | 4/2014 | Hamilton | |
| 2014/0101628 A1 | 4/2014 | Almog | |
| 2014/0109072 A1 | 4/2014 | Lang et al. | |
| 2014/0109115 A1 | 4/2014 | Low | |
| 2014/0109177 A1 | 4/2014 | Barton et al. | |
| 2014/0156823 A1 | 6/2014 | Liu | |
| 2014/0181715 A1 | 6/2014 | Axelrod | |
| 2014/0187228 A1 | 7/2014 | Fisher | |
| 2014/0240122 A1 | 8/2014 | Roberts | |
| 2014/0257058 A1 | 9/2014 | Clarysse et al. | |
| 2014/0257852 A1 | 9/2014 | Walker et al. | |
| 2014/0273913 A1 | 9/2014 | Michel | |
| 2014/0278536 A1 | 9/2014 | Zhang | |
| 2014/0282061 A1 | 9/2014 | Wheatley et al. | |
| 2014/0297311 A1 | 10/2014 | Jackson | |
| 2014/0309868 A1 | 10/2014 | Ricci | |
| 2014/0358482 A1 | 12/2014 | Sehgal | |
| 2014/0365961 A1 | 12/2014 | Lefor et al. | |
| 2015/0019342 A1 | 1/2015 | Gupta | |
| 2015/0025917 A1 | 1/2015 | Stempora | |
| 2015/0025997 A1 | 1/2015 | Tilenius et al. | |
| 2015/0056589 A1 | 2/2015 | Zhang et al. | |
| 2015/0074635 A1 | 3/2015 | Margiotta | |
| 2015/0089224 A1 | 3/2015 | Beckman | |
| 2015/0135160 A1 | 5/2015 | Gauvin | |
| 2015/0143470 A1 | 5/2015 | Stiekes et al. | |
| 2015/0148061 A1 | 5/2015 | Koukoumidis | |
| 2015/0154002 A1 | 6/2015 | Weinstein et al. | |
| 2015/0163121 A1 | 6/2015 | Mahaffey | |
| 2015/0199490 A1 | 7/2015 | Iancu et al. | |
| 2015/0294090 A1 | 10/2015 | Kodiyan | |
| 2015/0297078 A1* | 10/2015 | Gross | A61B 5/7275 340/870.07 |
| 2015/0352363 A1 | 12/2015 | McIntyre et al. | |
| 2015/0356701 A1 | 12/2015 | Gandy | |
| 2016/0058287 A1 | 3/2016 | Dyell | |
| 2016/0086297 A1 | 3/2016 | Dettinger et al. | |
| 2016/0092339 A1 | 3/2016 | Straub | |
| 2016/0189317 A1 | 6/2016 | Papandrea | |
| 2016/0234624 A1 | 8/2016 | Riva et al. | |
| 2017/0011200 A1 | 1/2017 | Arshad et al. | |
| 2017/0020444 A1 | 1/2017 | Lurie | |
| 2017/0048215 A1 | 2/2017 | Straub | |
| 2017/0124276 A1 | 5/2017 | Tee | |
| 2017/0132395 A1 | 5/2017 | Futch | |
| 2017/0220751 A1 | 8/2017 | Davis et al. | |
| 2017/0303187 A1 | 10/2017 | Crouthamel et al. | |
| 2017/0329483 A1 | 11/2017 | Jann et al. | |
| 2017/0329500 A1 | 11/2017 | Grammatikakis et al. | |
| 2017/0330297 A1 | 11/2017 | Cronin et al. | |
| 2017/0344895 A1 | 11/2017 | Roy | |
| 2017/0374178 A1 | 12/2017 | Sharma et al. | |
| 2018/0096590 A1* | 4/2018 | Grubis | A61B 5/0022 |
| 2018/0121187 A1 | 5/2018 | Jain et al. | |
| 2018/0197624 A1 | 7/2018 | Robaina et al. | |
| 2018/0232492 A1 | 8/2018 | Al-Alul et al. | |
| 2018/0247713 A1* | 8/2018 | Rothman | A61B 5/02055 |
| 2018/0308569 A1 | 10/2018 | Luellen | |
| 2019/0019581 A1 | 1/2019 | Vaughan et al. | |
| 2019/0026663 A1 | 1/2019 | Homeyer et al. | |
| 2019/0043501 A1 | 2/2019 | Ramaci | |
| 2019/0043610 A1 | 2/2019 | Vaughan | |
| 2019/0043619 A1 | 2/2019 | Vaughan et al. | |
| 2019/0074080 A1 | 3/2019 | Appelbaum et al. | |
| 2019/0172588 A1 | 6/2019 | Tran et al. | |
| 2019/0180862 A1 | 6/2019 | Wisser et al. | |
| 2019/0207814 A1 | 7/2019 | Jain et al. | |
| 2019/0214116 A1 | 7/2019 | Eberting | |
| 2019/0243944 A1 | 8/2019 | Jain et al. | |
| 2019/0286086 A1 | 9/2019 | Gardner et al. | |
| 2019/0313934 A1 | 10/2019 | Lee et al. | |
| 2019/0320310 A1 | 10/2019 | Horelik et al. | |
| 2020/0019995 A1 | 1/2020 | Krishnan et al. | |
| 2020/0050330 A1 | 2/2020 | Schilling et al. | |
| 2020/0112479 A1 | 4/2020 | Jain et al. | |
| 2020/0119986 A1 | 4/2020 | Jain et al. | |
| 2020/0131581 A1 | 4/2020 | Jain et al. | |
| 2020/0241859 A1 | 7/2020 | Jain et al. | |
| 2020/0241860 A1 | 7/2020 | Jain et al. | |
| 2020/0278852 A1 | 9/2020 | Jain et al. | |
| 2020/0348919 A1 | 11/2020 | Jain | |
| 2020/0356353 A1 | 11/2020 | Jain | |
| 2021/0026615 A1 | 1/2021 | Jain | |

FOREIGN PATENT DOCUMENTS

| | | | | |
|---|---|---|---|---|
| WO | WO 2012078753 | 6/2012 | | |
| WO | WO 2014087296 | 6/2014 | | |
| WO | WO-2014087296 A1 * | 6/2014 | | A61B 5/0002 |
| WO | WO 2016161416 | 10/2016 | | |
| WO | WO 2017106770 | 6/2017 | | |

OTHER PUBLICATIONS

[No Author Listed] "Digital therapeutics," Wikipedia, Nov. 20, 2017, [retrieved on Jan. 2, 2018], retrieved from: URL <https://en.wikipedia.org/wiki/Digital_therapeutics>, 4 pages.

[No Author] "Methods for JITAIs Just in Time Adaptive Intervention," 2016, Nov. 9, 2016, [retreieved on Nov. 9, 16], from the internet <https://community.isr.umich.edu/public/Default.aspx?alias=community.isr.umich.edu/public/jitai&>.

[No Author] "Methods for JITAIs Just in Time Adaptive Intervention," Nov. 9, 2016, retrieved on Nov. 9, 2016, retrieved from URL<https://community.isr.umich.edu/public/Default.aspx?alias=community.isr.umich.edu/public/jitai&>, 1 page.

[No Author], "KhanAcademic.org," retrieved on May 12, 2017, retrieved from URL<http://www.khanacademic.org>, 1 page.

Airwatch: "AirWatch Enterprise Mobility Management Demo," YouTube, Jul. 22, 2014, retrieved on May 3, 2017, retrieved from URL <https://www.youtube.com/watch?v=ucV1n4-tgk>, 1 page.

Airwatch: "Airwatch Laptop Management Demo," YouTube, Oct. 3, 2014, retrieved on May 3, 2017, retrieved from URL<https://www.youtube.com/watch?v=3gHfmdVZECM>, 1 page.

Braun et al., "Cancer Patient Navigator Tasks across the Cancer Care Continuum," J Health Care Poor Underserved, Feb. 1, 2012, 23(1):398-413.

Conner, "Experience sampling and ecological momentary assessment with mobile phones," 2015—http://www.otago.ac.nz/psychology/otago047475.pdf.

Conner, "Experience Sampling and Ecological Momentary Assessment with Mobile Phones," 2015, retrieved on May 3, 2017, retrieved from URL<http://www.otago.ac.nz/psychology/otago047475.pdf>, 4 pages.

Ece-Research-unm.edu [online], "Introduction to Lab VIEW: Six-Hour Course", published on Aug. 15, 2005, retrieved on Jul. 21, 2021, retrieved from URL<http://ece-research.unm.edu/jimp/415/labview/LV_Intro_Six_Hours.pdf>, 118 pages.

Egr-msu.edu [online], "Introduction to LabVIEW", published on Dec. 17, 2008, retrieved on Jul. 21, 2021, retrieved from URL<https://www.egr.msu.edu/~hashsham/courses/ene806/docs/LabView%20Introduction.pdf>, 30 pages.

Farr, "Can "Digital Therapeutics" Be as Good as Drugs?," MIT Technology Review, Apr. 7, 2017, [retrieved on Jan. 2, 2018], retrieved from: URL <https://www.technologyreview.com/s/604053/can-digital-therapeutics-be-as-good-as-drugs/>, 8 pages.

Fletcher et al., "Wearable Sensor Platform and Mobile Application for Use in Cognitive Behavioral Therapy for Drug Addiction and PTSD", 33rd Annual International Conference of the IEEE EMBS, 2011.

Guyot, "Apple's ResearchKit: Our Complete Overview," Mar. 9, 2015, retrieved on Mar. 30, 2020, retrieved from URL<https://www.macstories.net/news/apples-researchkit-our-complete-overview/>, 8 pages.

(56) References Cited

OTHER PUBLICATIONS

Henze et al., "Push the study to the App store: evaluating off-screen visualizations for maps in the android market," Proceedings of the 12th Conference on Human-Computer Interaction with Mobile Devices and Services, Lisbon, Portugal, Sep. 7-10, 2010, 373-374.
Heron, "Ecological Momentary Intervention [EMI]: Incorporating mobile technology into a disordered eating treatment program for college women," Psychology—Dissertations, paper 157, 2011.
http://www.khanacademic.org, [online], "Khan Academy," May 12, 2017, retrieved on Jan. 2, 2018, retrieved from URL <Khanacademic.org>, 1 page.
Lunn et al., "Using Mobile Technology to Engage Sexual and Gender Minorities in Clinical Research," Plos One, May 2, 2019, 14(5), 19 pages.
Matthews, "Johns Hopkins Researchers to Use Apple Watch Data to Study Epilepsy," Oct. 15, 2015, retrieved on Mar. 30, 2020, retrieved from URL<https://hub.jhu.edu/2015/10/15/apple-watch-epi-watch/>, 3 pages.
Milward, "Ecological momentary assessment," Jul. 2015, [retrieved on May 12, 2017], from the internet <https://www.addiction-ssa.org/commentary/emerging-research-methods-series-ecological-momentary-assessment>, 3 pages.
Milward, "Ecological momentary assessment," Jul. 2015, retrieved on May 12, 2017, retrieved from URL <https://www.addiction-ssa.org/commentary/emerging-research-methods-series-ecological-momentary-assessment>, 3 pages.
NI.com [online], "LabVIEW: Getting Started with LabVIEW", published on Jun. 15, 2013, retrieved on Jul. 21, 2021, retrieved from URL<https://www.ni.com/pdf/manuals/373427j.pdf>, 89 pages.
Pogue, "Apple's First 5 Health ResearchKit Apps in Brief," Jul. 1, 2015, retreived on Mar. 30, 2020, retrieved from URL<https://www.scientificamerican.com/article/pogue-apples-first-5-health-researchkit-apps-in-brief/>, 4 pages.
Runyan et al., "Virtues, ecological momentary assessment/intervention and smartphone technology," Front Psychol, 2015;6:481.
Runyan et al., "Virtues, ecological momentary assessment/intervention and smartphone technology," Frontiers in Psychology, May 2015, 6:481, 24 pages.
Shockney, "The Value of Patient Navigators as Members of the Multidisciplinary Oncology Care Team," 2017 ASCO Annual Meeting, ASCO Daily News, Jun. 6, 2016, [retrieved on Jan. 2, 2018], retrieved from: URL <https://am.asco.org/value-patient-navigators-members-multidisciplinary-oncology-care-team>, 3 pages.
Simon, "Patient Navigators Help Cancer Patients Manage Care," American Cancer Society, Feb. 24, 2017, [retrieved on Jan. 2, 2018], retrieved from: URL <https://www.cancer.org/latest-news/navigators-help-cancer-patients-manage-their-care.html>, 4 pages.
Taivan et al., "Application Diversity in Open Display Networks," Proceedings of the International Symposium on Pervasive Displays, Copenhagen, Denmark, Jun. 2014, 68-73.
Teems, "Automated Patient Navigation: Commission on Cancer and Other Requirements," Cordata Healthcare Innovations; Cordata Blog, Oct. 13, 2014, [retrieved on Jan. 2, 2018], retrieved from: URL <http://www.cordatahealth.com/blog/automated-patient-navigation-commission-on-cancer-and-other-requirements>, 4 pages.
Tourous et al., "Empowering the Digital Therapeutic Relationship: Virtual Clinics for Digital Health Interventions," NPJ Digital Medicine, May 2018, 1(16):1-3.
West et al., "There's an App for That: Content Analysis of Paid Health and Fitness Apps," Journal of Medical Internet Research, May-Jun. 2012, 14(3): e72, 12 pages.
Wikipedia.org [online], "LabVIEW", published on Jan. 11, 2019, retrieved on Jul. 21, 2021, retrieved from URL<https://web.archive.org/web/20190111021239/https:/en.wikipedia.org/wiki/LabVIEW>, 10 pages.
Notice of Allowance in U.S. Appl. No. 16/264,769, dated Apr. 21, 2020, 12 pages.
Notice of Allowance in U.S. Appl. No. 16/266,516, dated Oct. 20, 2021, 20 pages.
Office Action in U.S. Appl. No. 16/264,769, dated Jun. 18, 2019, 18 pages.
Office Action in U.S. Appl. No. 16/264,769, dated Oct. 11, 2019, 24 pages.
Office Action in U.S. Appl. No. 16/266,516, dated May 10, 2021, 15 pages.
Office Action in U.S. Appl. No. 17/375,791, dated Sep. 7, 2023, 28 pages.
Non-Final Office Action in U.S. Appl. No. 17/385,351, dated Oct. 5, 2023, 23 pages.

\* cited by examiner

CREATING AND TESTING DIGITAL BIO-MARKERS BASED ON GENETIC AND PHENOTYPIC DATA FOR THERAPEUTIC INTERVENTIONS AND CLINICAL TRIALS

CROSS-REFERENCE TO RELATED APPLICATIONS

This application is a continuation of U.S. application Ser. No. 16/266,516, filed Feb. 4, 2019, now pending, which is a continuation of U.S. application Ser. No. 16/264,769, filed Feb. 1, 2019, now U.S. Pat. No. 10,762,990, all of which are incorporated by reference.

BACKGROUND

Individuals, healthcare providers, researchers, and others may seek to collect and analyze large amounts of data from a variety of sources to study, monitor, or improve health; study, monitor, or improve healthcare services; conduct research; or make advances in therapies. But tools for collecting and analyzing large amounts of data from a variety of sources are lacking, as are tools for sharing related information.

Managing the interpretation of data and identifying markers for various health states can be difficult. The amount of data, types of data, or real-time processing strain may be too large for systems to handle. The analysis or reporting may be too regimented or restricted to a specific path, which makes changes difficult to implement and alternate hypotheses burdensome to test. Furthermore, there is no easy way to share data, methodologies, processes, configurations, algorithms, interpretations, and results among studies, among users, or across different scientific fields.

Current strategies for collecting data from numerous subjects, monitoring health status, and providing guidance to subjects on adhering to a therapy plan suffer from inflexibility. Current systems are designed to deploy a specific therapy plan, and they cannot identify new markers, or adapt markers to identify new therapeutics. Other systems may provide some flexibility in collecting data, but only if a user is capable of complex coding techniques.

Other systems offer unidirectional data migration, with hard-coded sensors, devices, and analyses. Other systems may offer processing of only stored data or real-time data, but not both. And often the data is obtained from only a single source.

Currently, data (e.g., baseline data) is first collected in a manner that is protocolized to match a specific model, and, then, after reviewing the data against the model, a new protocol is developed to collect further data and compare. This cycle repeats until a discovery is made, but it can take years to develop the protocol, modify the solution to aggregate the information, and then compare the results to the developed model to confirm whether the findings yield a level of precision required for investigatory trials of new pharmaceuticals, medical devices, and therapies. There exists a need for systems and methods to allow new markers and refined markers to be modeled and identified, to encompass the use of data from a variety of sources, to provide readily adaptable and reconfigurable analysis and reporting, to allow the sharing of information among users and/or subjects, and to facilitate the application of interventions. There exists a need for systems with bidirectional configurability; soft-coded formulaic re-configurability; the ability to process both real-time and stored data; the ability to test configurations; the ability to use predefined and/or configurable expressions; and the ability to collaborate and share data, workbooks, and expressions in a way that can be adapted and improved upon.

The disclosure presented herein addresses these and other problems of current systems.

DESCRIPTION

Figure 1:
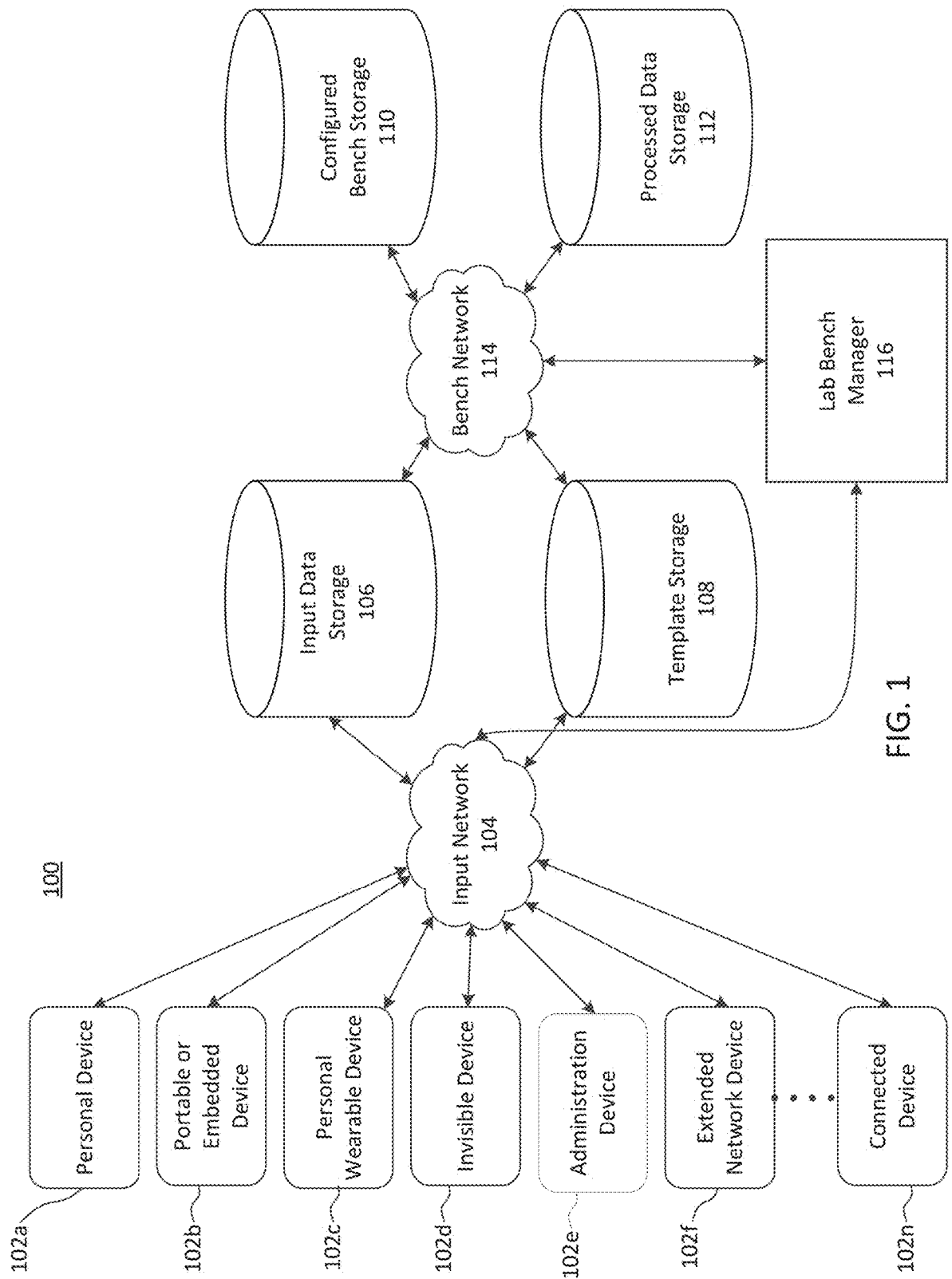
FIG. 1 is a diagram of an exemplary system for collecting, analyzing, and sharing data and information, consistent with disclosed embodiments.

The disclosure provides tools for collecting and analyzing large amounts of data from a variety of sources, as well as tools for sharing related information. In some embodiments, the disclosed systems provide a network of computers, comprised of a manager, a set of configuration files that specify an array of collaboration needs in building a computerized tool that can adaptively collect, analyze, and report large amounts of data from a variety of data sources, allowing the system to identify markers. In some embodiments, the disclosed systems include connected systems for delivering therapies and pharmaceutical treatments and for identifying and reporting scientific discoveries. Embodiments include systems and methods for receiving data, carrying out processes, and/or generating outputs. Some embodiments include systems and methods for interpreting received data; balancing system resource needs by adjusting inputs based on baselined outputs; carrying out measurement and collaboration methodologies, processes, configurations, algorithms, and/or interpretations; and/or generating outputs. Embodiments may be used to study or monitor health, improve health, study or monitor healthcare services, improve healthcare services, conduct research, and/or make advances in treatments or therapies. Embodiments may be used in digital health, digital therapeutics, precision medicine, and/or personalized medicine.

Some embodiments are systems, such as systems for detecting, generating, transmitting, and/or updating an output; systems for detecting, generating, transmitting, and/or updating a marker; and reconfigurable multi-manager observation systems. Some embodiments are systems with one or more memory units for storing instructions and one or more processors for executing the instructions to perform operations. In some embodiments, the system is reconfigurable and/or adaptable. In some embodiments, the system can be templated for deeper, more difficult omic-related discoveries that can evolve over time either through direct manipulation or machine learning hooks.

Some embodiments are methods, such as methods for detecting, generating, transmitting, and/or updating an output; methods for detecting, generating, transmitting, and/or updating a marker; and methods for reconfigurable multi-manager observation. Some embodiments are methods involving systems with one or more memory units for storing instructions and one or more processors for executing the instructions to perform operations. In some embodiments, the method involves a system that is reconfigurable and/or adaptable. In some embodiments, the method involves a system that can be templated for deeper more difficult omic-related discoveries that can evolve over time either through direct manipulation or machine learning hooks. Some embodiments are computer readable media that contain instructions for performing a disclosed method.

Some embodiments involve data associated with a subject. In some embodiments, the subject is human. In some embodiments, the subject includes one or more individuals. In some embodiments, the subject is a study candidate, a study participant, a patient, a group of study candidates, a group of study participants, a group of patients, and/or a community. For example, omic data may be related to many individuals. Omic-related studies, and the data related to those studies, may identify and/or relate to an individual and/or multiple individuals. A subject may knowingly or unknowingly provide data.

Some embodiments involve data associated with the surroundings, situations, or environment, e.g., the surroundings, situations, or environments of a subject.

Some embodiments involve data provided by a third party but relating to a subject. Data associated with a subject may be provided by a third party intentionally or actively. For example, a health care provider may intentionally submit records for a subject, or a friend of a subject may intentionally answer questions about a subject. As another example, a family member of a subject may intentionally agree to have her health data monitored, wherein that data is then associated with the subject. Data associated with a subject may also be provided by a third party unknowingly and/or without knowledge of the specific subject to which the data will be associated. For example, third parties interacting in an environment associated with a subject may unknowingly provide data that is then associated with the subject.

In some embodiments, the system is used by and/or the method is performed by a user. A user may, for example, define controls, permissions, and requests, and/or administer support for data deliveries. In some embodiments, the user includes one or more individuals. In some embodiments, the user may be, for example, a researcher, a health care provider (e.g., a doctor, a nurse, a practitioner of non-traditional medicine), an insurance agent, a group of researchers, a group of health care providers, a group of insurance agents, or an entity (e.g., a university, hospital, insurance company, and/or one or more individuals employed by or operating as agents of an entity). In some embodiments, the user may be a system. For example, another system may be programmatically designed to operate the disclosed system. Such an example may include a commercially purchased sensor that publishes community physiological, behavioral, and environmental data, wherein the sensor is acting on behalf of an individual installing the sensor, and the sensor interfaces with and operates the disclosed system. In some embodiments, the other system may include machine learning to provide automatic adaptation to the needs of a sensor network in order to deliver the needs of the anticipated human user or subject.

In some embodiments, the subject and the user are different. In some embodiments, the subject and the user are the same (e.g., an individual tracking her own data) or overlap (e.g., a researcher tracking her own data and the data of several other individuals).

Some embodiments involve data having various data collection parameters. Some embodiments include data collection parameters that include modifiable configurations to a sensor or a sensor network behavior, e.g., affecting how data is interpreted, collected, and/or shared through a server data input network. In some embodiments, a data collection parameter is a sample rate of data collection (e.g., frequency of collection, duty cycle or collection timing, publishing schedule, publishing interval). In some embodiments, a data collection parameter is a quality of service (QoS) parameter. In some embodiments, a data collection parameter is the number of times data is collected (e.g., duplicate, triplicate, taken again if a value is outside a range, maximum number of collections reached for the day). In some embodiments, a data collection parameter is a type of data collected. In some embodiments, a data collection parameter is a data type classifier, a group of classifiers, and/or a hardware type related to a classifier. In some embodiments, a data collection parameter is a setting. In some embodiments, a data collection parameter is a configuration or control to a hardware or software setting (e.g., a hardware power cycle, a visible light to be enabled or disabled during sampling, noise generating sources to be enabled or disabled during sampling). Some embodiments involve receiving data that is live, prerecorded, and/or preselected. Some embodiments involve receiving data that is live, prerecorded, and/or preselected over a period of time, in the past, present, or to be completed in the future.

Data may be collected in a variety of ways. For example, in some embodiments, data may be obtained from personal devices (e.g., mobile smartphones, tablets, laptops, desktop machines), portable or embedded devices (e.g., shared hardware, kiosks, hubs, set top boxes, navigation systems), personal wearable devices (e.g., wearables for on-the-body sensing through a removable device such as a watch or patch, wearables for in-the-body sensing through an ingestible or implantable), invisible devices (e.g., invisibles for passively sensed data from environmentally placed sensors capable of recording physiological, behavioral, and/or environmental data), administration devices (e.g., an insulin-injecting device, an intravenous delivery device, a wearable patch configured to administer or deliver a drug), extended network devices (e.g., medical record systems), and/or any connected device.

A device, as used in this disclosure, is to be interpreted broadly to encompass both self-contained physical units that provide a function and distributed systems that provide a function. For example, a serverless reporting system that provides data can be considered a device, just as a mobile phone, computer, or smartwatch may be considered a device.

In some embodiments, a personal device may reside in a subject's possession; provide access to information, permission, or requests; and/or allow the ability to permit access across a suite of sensors, sensor networks, and/or connected network interfaces. The personal device may include visible access to information collected in accordance with privacy and terms of service. In some embodiments, a personal device may receive additional configurations. These configurations may apply to connected sensors and sensor networks in order to act as a manager of the server data input network needs. These configurations may also be able to modify the personal device and the behaviors of sensors and sensor networks associated with the personal device. In some embodiments, these configurations allow a subject to receive instructions on deployment issues and be instructed to resolve problems as they arise. In some embodiments, a personal device may act as a sensor as data that is collected from it may be shared to a server data input network.

In some embodiments, a portable or embedded device may reside in an environment (e.g., a home, a car, a community); provide a subject access to information, permission, or requests; and/or allow the ability to permit access across a suite of sensors, sensor networks, and/or connected network interfaces. A subject may directly interact with a portable or embedded device, but such functionality is not required. In some embodiments, this interaction may occur through a kiosk or a smartphone application that allows the subject to control specific settings or configurations specific to permissions, server network or sensor network configurations, or notifications and transparency in subject involvement. A portable or embedded device may also serve as a gateway or a pass-through of information to sensors, for example in a sensor network. AMAZON ECHO DOT with ALEXA, SAMSUNG SMARTTHINGS, and GOOGLE HOME are examples of hubs portable indirect client hardware. APPLE TV with HOMEKIT is an example of a set top box that can connect to sensors in a home. For example, an ALEXA may be combined with a car with GPS navigation systems such as GARMIN, and with a device collecting heart rate information, and machine learning algorithms could, for example, adjust the speed of the car based on fear and excitement in smart vehicles such as TESLA.

In some embodiments, a personal wearable device may reside on or in the body of a subject. In some embodiments, a personal wearable device may be a personal device, a wearable, an ingestible, or an implantable. In some embodiments where the personal wearable device is a personal device, a subject may interact with the equipment when a measurement is requested or an update is desired, such as a cardiac related sensor like a blood pressure cuff or ECG, a respiration related sensor such as a spirometer or pulse oximeter, a neurological related sensor such as a EEG, or a physical body sensor such as body temp sensor or weight sensor. In some embodiments, a subject may regularly interact with a personal wearable device for a time period (e.g., hours, days) during a specific task (e.g., exercising, sleeping, eating, traveling, obtaining a baseline of measurements). In some embodiments, the personal wearable device may be in the form of a watch, a patch, eyeglasses, or an article of clothing. In some embodiments where the personal wearable device is an ingestible, a subject may swallow a sensor for periodic in-body readings of metabolic function, digestion, and/or fluid composition makeup. In some embodiments, the personal wearable device is an implantable. For example, a subject may be surgically implanted with a sensor in the form of a tattoo in the dermis, a continuous glucose sensor in the subcutaneous, an intramuscular sensor for artificial limb recipients, an intravenous sensor for infusion monitoring, or an organ specific observational sensor.

In some embodiments, an invisible device may reside in an environment (e.g., a home, a car, a community). In some embodiments, an invisible may comprise sensors that collect physiological, behavioral, and/or environmental data without requiring interaction, approval, notification, and/or subject-driven configurations between a sensor and a subject. For example, an invisible device may comprise a sensor in a bed to detect sleeping conditions or a sensor in a wall to detect positioning or physiological signals of a subject.

A source of data may be categorized as one or more of the foregoing list of exemplary data sources. For example, a mobile phone may be considered a personal device when a subject is carrying it and it is recording location data, but it may be considered an invisible device when it is placed on the bed during sleeping to capture, using an accelerometer, vibrations in the bed or when the microphone or light sensor is used to pick up ambient sound or light. A mobile phone may be considered a portable device when it requires interaction to start the recording of data. A mobile phone may also may be considered a personal wearable device when a subject places it in an armband to monitor an activity (e.g., running).

A variety of types of data may be used with the disclosed systems and methods. For example, in some embodiments, data may reflect a wide variety of health conditions and behaviors, including those relating to biological, physical, mental, emotional, environmental, social, and other inputs. In some embodiments, data may be omics data (e.g., data relating to genomics, proteomics, pharmacogenomics, epigenomics), cardiac-related data (e.g., data from ECG monitors, heart rate monitors, blood pressure monitors), respiratory-related data (e.g., data from spirometers, pulse oximeters), neurological-related data (e.g. data from EEG monitors), behavior data (e.g., data on movement patterns, gait, social avoidance), substance use data (e.g., data regarding use of alcohol, medication, recreational drug, tobacco), sleep data (e.g., data relating to motion, heart rate, body temperature, perspiration, breathing, ambient light, ambient sound, ambient temperature), exercise data (e.g., data related to performance, distance covered, activity, maximal oxygen consumption), physical activity data (e.g., data regarding step counts, heart rate, flights climbed, altitude, data from a fitness tracker), mood data (e.g., data relating to happiness, depression, brief mood introspection score), biologically sampled or derived data (e.g., data related to blood, urine, saliva, breath sample, skin scrape, hormone level, glucose level, a breathalyzer, DNA, perspiration), lab or diagnostic data (e.g., assay data, blood test results, tissue sample results, endocrine panel results), positioning or location data (e.g., GPS data, gyroscope data, altimeter data, accelerometer data, linear acceleration data, received signal strength indicator from an emitter such as a WIFI access point, data from a BLUETOOTH sensor or sensor network, data from a cellular tower), environmental data (e.g., air quality data, ozone data, weather data, water-quality data), vehicle data (e.g., speed, location, amount of time driving, mood while driving, environmental data in the car), drug data (e.g., prescription information, pharmacological data). Data may be categorized as one or more of the foregoing list of exemplary data types.

A variety of processes may be included in the disclosed methods or performed by the disclosed systems. For example, some embodiments involve selecting one or more variable classes. A variable class relates to a variety of related received data. In some embodiments, the variable class may relate to, for example, sleep, diet, exercise, activity, substance use (e.g., alcohol use, medication use, recreational drug use, tobacco use), mood (e.g., happiness, depression), and/or biological functioning (heart, blood pressure, breathing). A variable class may also relate to one or more other types of data as described above. For example, a heart variable class may include an active heart rate data value with or without display related sample holds; averaged heart rate over a number of samples; a peak heart rate over a specified duration; a resting heart rate data value over a specified duration or day to day; a raw beat to beat R-R interval data value; data collection method or process such as electrically recorded ECG related signal data; light sampled photoplethysmography data; audible collected oscillometric or stethoscope related data; artifacts such as motion, atrial fibrillation, tachycardia or bradycardia related detection; arrhythmia; heart murmur data; or other heart data.

A variable class may be a predictor variable class and/or an outcome variable class based on its function within a model. For example, in some embodiments, a model may be that a sleep variable, an exercise variable, and a diet variable together predict or provide information about a blood pressure variable. In such example, sleep, exercise, and diet are predictor variable classes, while blood pressure is an outcome variable class. In other embodiments, a model may be that a blood pressure variable, a diet variable, a sleep variable, and an exercise variable predict or provide information about a cancer survivorship variable. In such example, blood pressure, diet, sleep, and exercise are predictor variable classes, while cancer survivorship is an outcome variable class.

A variety of outputs may be generated using the disclosed systems and methods. An output may be the final result of one or more processes, or the output of one process may be used as an input of a further process. Some embodiments involve generating an output that is based on data, a rule, a relationship, and/or a different output. Some embodiments involve generating an output that is associated with a variable class.

Some embodiments involve generating an output using one or more expressions (e.g., rules, methods, formulas, processes, algorithms, configurations, interpretations, models). Some embodiments involve expressions that are rule-based algorithms, machine-learning models, and/or statistical models. Some embodiments use expressions that can be reused across a group of users. In some embodiments the expression may involve using a rule such as a predictor rule, an outcome rule, and/or a marker rule. Some embodiments involve using a rule such as measuring data as a moving average or combining two data sources. In some embodiments, an expression may involve processing a specific sequence or order of data. In some embodiments, a formula may specify an overall equation and process capability components for real-world factors including variance adjustments and bias corrections. In some embodiments, an expression may involve managing processes and controls anticipated by the subject or delivered to the user for further collection and processing. Some embodiments may involve performing an algorithmic analysis. Some embodiments may specify configurations of sensors such as sampling needs, QoS, and/or control driven enablement for turning on or off remote hardware. Some embodiments may specify expected interpretations from a baseline or theory of operation. Some embodiments involve selecting a subset of data from data received.

Some embodiments involve generating scores as output, wherein a score is, for example, a numerical value, a relative numerical value, a grade, or a percentage. Examples of scores that may be generated by the disclosed systems and methods include, for example, a predictor score, an outcome score, a marker score, and/or a therapy adherence score. A predictor score is an estimate of a predictor variable based on data and a predictor rule. For example, a predictor score of "72" representing an estimate of a subject's resting heart rate as a quantified beats per minute or a scalar qualified range may be calculated using, for example, heart rate data and motion data, where the motion data assists in interpreting whether a person is at rest, and based on a predictor rule that averages the time between heart beats over all periods in the previous 48 hours in which a person is at rest for longer than five minutes. This predictor score may be a sliding score and can be recalculated, for example, every 24 hours based on the previous 48 hours of data. An outcome score is an estimate of an outcome variable based on data and an outcome rule. An outcome score differs from a predictor score based on its function in a model. Thus, the estimated resting heart rate of "72" described above may be considered a predictor score when it is used to predict an outcome, e.g., when the estimated resting heart rate score of "72", an exercise score, and a diet score together predict a sleep variable such as sleep duration or quality. But the estimated resting heart rate of "72" may be considered an outcome score when it is the score for the predicted outcome, e.g., when a sleep score, an exercise score, and a diet score predict an estimated resting heart rate increase, decrease, or leveling to "72.".

Some embodiments may involve a score that represents a value for data, such as a blood pressure score. Some embodiments may involve a score that represents a combination of other scores, for example, a heart score that represents a combination of heart rate and blood pressure scores. In some embodiments, the score may be the data itself. For example, a blood pressure data may be 120/80 millimeter of mercury (mmHg) and the blood pressure score may be 120/80. As another example, a sleep duration data may be 6.5 hours and the sleep duration score may be "9" of a possible "10." The score may take into account several factors when calculating qualified data values and quantified data values by varying expressions and inputs inferred within the system.

A marker score represents a combination of one or more predictor scores and is based on a marker rule. For example, a marker score for a level of stress may be based on a sleep quality score and a blood pressure score, and the marker rule may be to normalize the scores, and then subtract the normalized sleep quality score from a normalized blood pressure score.

Some embodiments involve generating a marker metric based on a marker score, an outcome score, and a marker relationship. A marker relationship is a relationship between a marker score and an outcome score (e.g., statistical relationship, a descriptive relationship, a model). For example, the relationship may be a linear regression between a marker score time series and an outcome score time series. In some embodiments, a marker metric is a correlation coefficient, such as a Pearson's correlation coefficient. In some embodiments, a marker metric is a regression result, such as linear, polynomial, or logistic. In some embodiments, a metric is an R-squared value.

For example, a marker metric may be "100% accurate" if the relationship between the calculated marker score and outcome score is one to one. As another example, a marker metric may be less than 100% accurate if, for example the marker score indicates that 4 hours of sleep indicates a 90% chance of afternoon drowsiness, but the outcome scores indicate that 4 hours of sleep have led to afternoon drowsiness for 10 of the last 10 instances (i.e., the calculated marker score does not have a one to one relationship to the outcome score).

Some embodiments may be used to detect, develop, generate, transmit, and/or update a marker. For example, some embodiments involve a marker that serves to identify, predict, or characterize a health condition or behavior. In some embodiments, a marker is a data-based indicator of a health status. In some embodiments, a marker is an evidence-based measurable digital marker that relates to physiological signals, either observed through measurable changes or collected through biosamples. In some embodiments, a marker's characteristic that is omic-discovery related (e.g. phenotyping) is observed as personalized characteristics of biosample data (e.g., as related to sleep monitored information). In some embodiments, a marker is an instance of a data collection (e.g., a detected heart beat murmur or single QRS complex). In some embodiments, a marker is a calculated value based on data collected over a period of time (e.g., a calculated resting heart rate based on data collected over a week). In some embodiments, a marker is associated with different types of data, such as heart, sleep, diet, social media, and activity. Data for a marker may be available when direct evidence of a health outcome is unavailable or not readily available. For example, in some embodiments, a marker of chronic stress may indicate a later health outcome of high blood pressure even while a patient is exhibiting normal blood pressure readings.

Some embodiments may involve one or more relationships. For example, some embodiments involve a marker relationship between a marker score and an outcome score. A relationship may, for example, be a statistical relationship, a descriptive relationship, or a model. A relationship may be quantified using, for example, statistical methods, machine learning methods, and/or user-defined methods. For example, some embodiments involve a relationship that is a linear regression between a marker score time series and an outcome score time series. In some embodiments, a relationship is tracked to provide a sign of a later health outcome.

Some embodiments involve multiple rounds of receiving data, carrying out one or more processes, and/or generating an output. For example, some embodiments involve receiving first data, carrying out one or more first processes, generating one or more first outputs, receiving second data, carrying out one or more second processes, and generating one or more second outputs. Some embodiments involve receiving one or more data, selecting one or more first variable classes based on the data, generating one or more first outputs, selecting one or more second variable classes based on the data, and generating one or more second outputs. Some embodiments involve receiving one or more first data, selecting one or more first variable classes based on the first data, generating one or more first outputs, receiving one or more second data, selecting one or more second variable classes based on the second data, and generating one or more second outputs. Some embodiments involve receiving one or more first data, selecting one or more first variable classes based on the first data, generating one or more first outputs, receiving one or more second data, the second data being selected based on the one or more first outputs, and generating one or more second outputs. Some embodiments involve receiving one or more first data, carrying out one or more first processes, generating one or more first outputs, generating one or more second outputs, and generating one or more third outputs.

In some embodiments, information can be transmitted and reprocessed multiple times as refinements are made to validate one or more outcomes and/or validate the accuracy of one or more markers.

Some embodiments involve determining whether a metric satisfies a criterion, such as a certain value for a goodness of fit or a threshold. For example, some embodiments may evaluate the goodness of fit to determine if it is chi-squared, Kolmogorov-Smirnov, Anderson-Darling, and/or a Shipiro-Wilk.

Some embodiments involve determining a likelihood of a health event based on the disclosed methods and/or using the disclosed systems. Some embodiments involve a cancer-related event, such as cancer relapse or cancer survivorship. Some embodiments involve a substance-related event such as drug use relapse or maintenance of sobriety for a period of time. Some embodiments involve a weight change, such as a weight loss or a weight gain. Some embodiments involve an episode, such as a depressive episode, a psychotic episode, or a panic attack. Some embodiments involve a heart attack, diabetic shock, an infectious illness, and/or a fever.

Some embodiments involve sending or transmitting a notification, a command, and/or recommendation in response to determinations made based on the disclosed methods and/or using the disclosed systems. Some embodiments involve sending or transmitting data or information to a healthcare provider, a social media system, a user, and/or a contact associated with a subject or user. Some embodiments involve sending or transmitting a command to update a rule, a data collection parameter, an output, and/or a relationship. Some embodiments involve sending or transmitting a command to generate, for example, an output. Some embodiments involve sending or transmitting a command to a device, such as a device to deliver a drug. In some embodiments, the command is to change drug administration.

Some embodiments involve making an update to, for example, a data collection parameter, a rule, a relationship, and/or an output, based on the results of using the disclosed methods and/or systems.

Some embodiments involve receiving a request, for example, to share data, an output, and/or a therapeutic recipe. Some embodiments involve receiving an instruction, such as an instruction to update, for example, a data collection parameter, a rule, a relationship, and/or an output.

Some embodiments involve storing, processing, and/or recording data, a rule, an output, and/or a therapeutic recipe.

Some embodiments involve one or more therapeutic recipes. A therapeutic recipe may include therapeutic activities for studying, monitoring, or improving a health condition or behavior. For example, some embodiments involve therapeutic recipes that involve a drug prescription, surgery support, an exercise regimen, a diet, a sleep schedule, and/or counseling. Some embodiments involve transmitting a therapeutic recipe to a device. Some embodiments involve transmitting a command to a device based on a therapeutic recipe. In some embodiments, a therapeutic recipe is developed by a researcher to monitor and/or study health. In some embodiments, a therapeutic recipe is provided or used by a healthcare provider to improve a patient's health. In some embodiments, a therapeutic recipe is updated or modified.

Some embodiments involve generating a workbook. In some embodiments, a workbook may allow a new model for a marker and internet-of-things (IoT) based configurations in the exchange of data, weighing usefulness and accuracy in determining accurate outcomes. In some embodiments, a workbook may be a file that defines a configuration of a marker. In some embodiments, a workbook may be sharable. Some embodiments involve assigning one or more privileges of a workbook, for example, to one or more manager accounts.

Some embodiments involve a visualization tool that can simplify a user's view of creating complex markers through layers of formulaic expressions.

Some embodiments are reconfigurable multi-manager observation systems comprising one or more memory units storing instructions, and one or more processors for executing the instructions to perform operations. In some embodiments, the operations comprise receiving data associated with a subject, the data having one or more data collection parameters; generating a metric based on the data; and sending, based on the metric, a command to update the data collection parameters. In some embodiments, the operations comprise receiving data associated with a subject, the data having one or more data collection parameters; generating a metric based on the data; and sending, based on the metric, a command to update the data collection parameters by changing at least one of a rate of data collection, a type of data collection, or a device setting. In some embodiments, the operations comprise receiving data associated with a subject, the data having one or more data collection parameters; generating a predictor score based on the data and a predictor rule; generating an outcome score based on the data and an outcome rule; generating a marker score based on the predictor score and a marker rule; generating a metric based on the data; and sending, based on at least one of the predictor score, the outcome score, the marker score, or the metric, a command to update the data collection parameters. In some embodiments, the operations comprise receiving data associated with a subject, the data having one or more data collection parameters; selecting a predictor variable class based on the data; generating a predictor score associated with the predictor variable class based on the data and a predictor rule; selecting an outcome variable class based on the data; generating an outcome score associated with the outcome variable class based on the data and an outcome rule; generating a marker score based on the predictor score and a marker rule; generating a metric based on the data; and sending, based on at least one of the predictor score, the outcome score, the marker score, or the metric, a command to update the data collection parameters.

In some embodiments, the operations comprise receiving data associated with a subject, the data having one or more data collection parameters; generating a metric based on the data; and sending, based on the metric, a command to a device associated with the subject, the device configured to deliver a drug to the subject, the command to the device comprising an instruction to change the administration of the drug. In some embodiments, the operations comprise receiving data associated with a subject, the data having one or more data collection parameters; generating a metric based on the data; and sending, based on the metric, a command to a device associated with the subject, the device configured to deliver a drug to the subject, the command to the device comprising an instruction to change the administration of the drug by increasing the amount of drug administered. In some embodiments, the operations comprise receiving data associated with a subject, the data having one or more data collection parameters; generating a predictor score based on the data and a predictor rule; generating an outcome score based on the data and an outcome rule; generating a marker score based on the predictor score and a marker rule; generating a metric based on the data; and sending, based on at least one of the predictor score, the outcome score, the marker score, or the metric, a command to a device associated with the subject, the device configured to deliver a drug to the subject, the command to the device comprising an instruction to change the administration of the drug. In some embodiments, the operations comprise receiving data associated with a subject, the data having one or more data collection parameters; selecting a predictor variable class based on the data; generating a predictor score associated with the predictor variable class based on the data and a predictor rule; selecting an outcome variable class based on the data; generating an outcome score associated with the outcome variable class based on the data and an outcome rule; generating a marker score based on the predictor score and a marker rule; generating a metric based on the data; and sending, based on at least one of the predictor score, the outcome score, the marker score, or the metric, a command to a device associated with the subject, the device configured to deliver a drug to the subject, the command to the device comprising an instruction to change the administration of the drug.

In some embodiments, the operations comprise receiving data associated with a subject, the data having one or more data collection parameters; generating a metric based on the data; and determining whether the metric satisfies a criterion. In some embodiments, the operations comprise receiving data associated with a subject, the data having one or more data collection parameters; generating a metric based on the data; determining whether the metric satisfies a criterion; and sending, based on the determination, a notification to at least one of a device associated with the subject, a health care provider system, a social media system, or a contact associated with the subject, wherein the notification comprises a statement of whether the metric satisfies the criterion. In some embodiments, the operations comprise receiving data associated with a subject, the data having one or more data collection parameters; generating a predictor score based on the data and a predictor rule; generating an outcome score based on the data and an outcome rule; generating a marker score based on the predictor score and a marker rule; generating a metric based on the data; and determining whether the metric satisfies a criterion. In some embodiments, the operations comprise receiving data associated with a subject, the data having one or more data collection parameters; selecting a predictor variable class based on the data; generating a predictor score associated with the predictor variable class based on the data and a predictor rule; selecting an outcome variable class based on the data; generating an outcome score associated with the outcome variable class based on the data and an outcome rule; generating a marker score based on the predictor score and a marker rule; generating a metric based on the data; and determining whether the metric satisfies a criterion.

In some embodiments, the operations comprise receiving data associated with a subject, the data having one or more data collection parameters; generating a metric based on the data; and determining, based on the metric, a likelihood of a health event. In some embodiments, the operations comprise receiving data associated with a subject, the data having one or more data collection parameters; generating a metric based on the data; and determining, based on the metric, a likelihood of a health event; and sending, based on the determination, a notification to at least one of a device associated with the subject, a health care provider system, a social media system, or a contact associated with the subject, wherein the notification comprises a statement of the likelihood of the health event. In some embodiments, the operations comprise receiving data associated with a subject, the data having one or more data collection parameters; generating a predictor score based on the data and a predictor rule; generating an outcome score based on the data and an outcome rule; generating a marker score based on the predictor score and a marker rule; generating a metric based on the data; and determining, based on at least one of the predictor score, the outcome score, the marker score, or the metric, a likelihood of a health event. In some embodiments, the operations comprise receiving data associated with a subject, the data having one or more data collection parameters; selecting a predictor variable class based on the data; generating a predictor score associated with the predictor variable class based on the data and a predictor rule; selecting an outcome variable class based on the data; generating an outcome score associated with the outcome variable class based on the data and an outcome rule; generating a marker score based on the predictor score and a marker rule; generating a metric based on the data; and determining, based on at least one of the predictor score, the outcome score, the marker score, or the metric, a likelihood of a health event.

In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; generating a metric based on the data and the therapeutic recipe; and sending, based on the metric, a command to update the data collection parameters. In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; generating a metric based on the data and the therapeutic recipe; and sending, based on the metric, a command to update the data collection parameters by changing at least one of a rate of data collection, a type of data collection, or a device setting. In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; generating a predictor score based on the data and a predictor rule; generating an outcome score based on the data and an outcome rule; generating a marker score based on the predictor score and a marker rule; generating a metric based on the outcome score, the marker score, and a marker relationship; and sending, based on at least one of the predictor score, the outcome score, the marker score, or the metric, a command to update the data collection parameters. In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; selecting a predictor variable class based on the data; generating a predictor score associated with the predictor variable class based on the data and a predictor rule; selecting an outcome variable class based on the data; generating an outcome score associated with the outcome variable class based on the data and an outcome rule; generating a marker score based on the predictor score and a marker rule; generating a metric based on the outcome score, the marker score, and a marker relationship; and sending, based on at least one of the predictor score, the outcome score, the marker score, or the metric, a command to update the data collection parameters.

In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; generating a therapy impact metric based on the data and the therapeutic recipe; and sending, based on the therapy impact metric, a command to update the data collection parameters. In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; generating a therapy impact metric based on the data and the therapeutic recipe; and sending, based on the therapy impact metric, a command to update the data collection parameters by changing at least one of a rate of data collection, a type of data collection, or a device setting. In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; generating a predictor score based on the data and a predictor rule; generating an outcome score based on the data and an outcome rule; generating a marker score based on the predictor score and a marker rule; generating a therapy impact metric based on the outcome score, the marker score, and a marker relationship; and sending, based on at least one of the predictor score, the outcome score, the marker score, or the therapy impact metric, a command to update the data collection parameters. In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; selecting a predictor variable class based on the data; generating a predictor score associated with the predictor variable class based on the data and a predictor rule; selecting an outcome variable class based on the data; generating an outcome score associated with the outcome variable class based on the data and an outcome rule; generating a marker score based on the predictor score and a marker rule; generating a therapy impact metric based on the outcome score, the marker score, and a marker relationship; and sending, based on at least one of the predictor score, the outcome score, the marker score, or the therapy impact metric, a command to update the data collection parameters.

In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; generating a therapy impact metric based on the data and the therapeutic recipe; and sending, based on the therapy impact metric, a revised command to the device, the revised command comprising a revised instruction to deliver the drug. In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; generating a therapy impact metric based on the data and the therapeutic recipe; and sending, based on the therapy impact metric, a revised command to the device, the revised command comprising a revised instruction to deliver the drug by increasing the amount of drug administered. In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; generating a predictor score based on the data and a predictor rule; generating an outcome score based on the data and an outcome rule; generating a marker score based on the predictor score and a marker rule; generating a therapy impact metric based on the outcome score, the marker score, and a marker relationship; and sending, based on at least one of the predictor score, the outcome score, the marker score, or the therapy impact metric, a revised command to the device, the revised command comprising a revised instruction to deliver the drug. In some embodiments, the operations comprise generating a therapeutic recipe comprising a therapeutic activity; transmitting the therapeutic recipe to a device associated with the subject; transmitting a command to the device, the device being configured to deliver a drug to the subject, the command comprising an instruction to deliver the drug; receiving data associated with a subject, the data having one or more data collection parameters; selecting a predictor variable class based on the data; generating a predictor score associated with the predictor variable class based on the data and a predictor rule; selecting an outcome variable class based on the data; generating an outcome score associated with the outcome variable class based on the data and an outcome rule; generating a marker score based on the predictor score and a marker rule; generating a therapy impact metric based on the outcome score, the marker score, and a marker relationship; and sending, based on at least one of the predictor score, the outcome score, the marker score, or the therapy impact metric, a revised command to the device, the revised command comprising a revised instruction to deliver the drug.

In some embodiments, the operations comprise generating a workbook; assigning a workbook privilege of the workbook to a manager account; receiving data associated with a subject, the data having one or more data collection parameters; generating a metric based on the data; and sending, based on the metric, a command to update the data collection parameters. In some embodiments, the operations comprise generating a workbook; assigning a workbook privilege of the workbook to a manager account; receiving data associated with a subject, the data having one or more data collection parameters; generating a metric based on the data; and sending, based on the metric, a command to update the data collection parameters by changing at least one of a rate of data collection, a type of data collection, or a device setting. In some embodiments, the operations comprise generating a workbook; assigning a workbook privilege of the workbook to a manager account; receiving data associated with a subject, the data having one or more data collection parameters; generating a predictor score based on the data and a predictor rule; generating an outcome score based on the data and an outcome rule; generating a marker score based on the predictor score and a marker rule; generating a metric based on the outcome score, the marker score, and a marker relationship; and sending, based on at least one of the predictor score, the outcome score, the marker score, or the metric, a command to update the data collection parameters. In some embodiments, the operations comprise generating a workbook; assigning a workbook privilege of the workbook to a manager account; receiving data associated with a subject, the data having one or more data collection parameters; selecting a predictor variable class based on the data; generating a predictor score associated with the predictor variable class based on the data and a predictor rule; selecting an outcome variable class based on the data; generating an outcome score associated with the outcome variable class based on the data and an outcome rule; generating a marker score based on the predictor score and a marker rule; generating a metric based on the outcome score, the marker score, and a marker relationship; and sending, based on at least one of the predictor score, the outcome score, the marker score, or the metric, a command to update the data collection parameters.

In some embodiments, the operations comprise generating a workbook; assigning a privilege of the workbook to a manager account; generating a therapeutic recipe comprising a therapeutic activity; storing the therapeutic recipe in the workbook; receiving, from the manager account, instructions to update the therapeutic recipe; updating the therapeutic recipe based on the instructions; and sending, based on the update to the therapeutic recipe, a command to update the data collection parameters. In some embodiments, the operations comprise generating a workbook; assigning a privilege of the workbook to a manager account; generating a therapeutic recipe comprising a therapeutic activity; storing the therapeutic recipe in the workbook; receiving, from the manager account, instructions to update the therapeutic recipe; updating the therapeutic recipe based on the instructions; and sending, based on the update to the therapeutic recipe, a command to update the data collection parameters, wherein the update to the data collection parameters comprise changing at least one of a rate of data collection, a type of data collection, or a device setting. In some embodiments, the operations comprise generating a workbook; assigning a first privilege of the workbook to a first manager account; generating a therapeutic recipe comprising a therapeutic activity; storing the therapeutic recipe in the workbook; receiving, from a device associated with a second manager account, a request to share the workbook; assigning a second privilege of the workbook to the second manager account; receiving, from the second manager account, instructions to update the therapeutic recipe; updating the therapeutic recipe based on the instructions; and sending, based on the update to the therapeutic recipe, a command to update the data collection parameters. In some embodiments, the operations comprise generating a workbook; assigning a first privilege of the workbook to a first manager account; generating a rule associated with the workbook; storing the rule in the workbook; generating a therapeutic recipe comprising a therapeutic activity; storing the therapeutic recipe in the workbook; receiving, from a device associated with a second manager account, a request to share the workbook; assigning a second privilege of the workbook to the second manager account; receiving, from the second manager account, instructions to update at least one of the rule or the therapeutic recipe; updating at least one of the rule or the therapeutic recipe based on the instructions; and sending, based on the update to the at least one of the rule or the therapeutic recipe, a command to update the data collection parameters.

FIG. 1 is a diagram of an exemplary system 100 for collecting, analyzing, and sharing data and information, consistent with disclosed embodiments. System 100 may include one or more components. System 100 may include, for example, personal device 102a, portable or embedded device 102b, personal wearable device 102c, invisible device 102d, administration device 102e, extended network device 102f, connected device 102n, input data storage 106, template storage 108, configured bench storage 110, processed data storage 112, and lab bench manager 116. System 100 may include one or more of each component, it may include only some of these components, and it may include other components not depicted in FIG. 1.

Components of system 100 may be arranged in various ways. Components of system 100 may, for example, be connected to each other through a network, e.g., input network 104 or bench network 114. System 100 may include one or more of each connection, it may include only one of these connections, and it may include other connections not depicted in FIG. 1.

Personal device 102a is a device that provides data for system 100. Personal device 102a may collect and/or transmit data about a subject and/or environment. Personal device 102a may have a dedicated subject (e.g., be used by and/or collect information for a single subject). Personal device 102a may include a subject-actionable interface and a programmatic interface. A subject actionable interface may allow the subject to interact using the device. A programmatic interface may allow the subject to interact using an alternate device. Personal device 102a may comprise one or more sensors and may be connected to one or more sensor networks. Personal device 102a may be, for example, a mobile device, a fitness-tracking device, a tablet, or a personal computer.

Personal device 102a may include hardware, software, and/or firmware. Personal device 102a may include one or more memory units for storing instructions and one or more processors for executing the instructions to perform operations.

Personal device 102a may be configured to detect and/or automatically connect to another device, such as portable or embedded device 102b, personal wearable device 102c, invisible device 102d, administration device 102e, extended network device 102f, or any other connected device 102n. Personal device 102a may connect to input network 104, as depicted in FIG. 1, or directly connect to lab bench manager 116 or one or more other components of system 100. Personal device 102a may be configured to transmit data and information to other components of system 100, for example, via input network 104.

Personal device 102a may connect to input network 104 or one or more other components of system 100 by a wireless connection and/or a wired connection. In some embodiments, a wireless connection includes a WI-FI communication connection, a BLUETOOTH communication connection, a LI-FI communication connection, a NEAR FIELD COMMUNICATION (NFC) connection, and/or an optical wireless communication connection. In some embodiments, a wired connection includes a UNIVERSAL SERIAL BUS (USB) connection, a FIREWIRE connection, an ethernet connection, and/or a cable connection.

Portable or embedded device 102b may be, for example, a kiosk, a hub, a set top box, a digital assistant, an internet television device, or a device configured to perform operations. In some embodiments, portable indirect device 102b includes an AMAZON ALEXA device or an APPLE TV device.

Portable or embedded device 102b may be located, for example, in a home, a workplace, a school, a community center, a public space, or a vehicle. Portable or embedded device 102b may serve as a gateway or a pass-through of data or information from an external device (not shown in FIG. 1) to one or more other components of system 100.

Portable or embedded device 102b may be associated with and/or provide data for multiple subjects. Portable or embedded device 102b may include one or more sensors and may be connected to one or more sensor networks. Portable or embedded device 102b may be configured to receive inputs, for example, via an interface (e.g., keyboard inputs, button inputs, audio inputs, touchscreen inputs, mouse inputs, other peripheral inputs). Portable or embedded device 102b may include a subject-actionable interface and a programmatic interface. A subject actionable interface may allow the subject to interact using the device. A programmatic interface may allow the subject to interact using an alternate device. In some embodiments, portable or embedded device 102b is configured to receive physiological data, environmental data, audio data, and/or other data.

Portable or embedded device 102b may include hardware, software, and/or firmware. Portable or embedded device 102b may include one or more memory units for storing instructions and one or more processors for executing the instructions to perform operations.

Portable or embedded device 102b may be configured to detect and/or automatically connect to another device, such as personal device 102a, personal wearable device 102c, invisible device 102d, administration device 102e, extended network device 102f, or any other connected device 102n. Portable or embedded device 102b may connect to input network 104, as depicted in FIG. 1, or directly connect to lab bench manager 116 or one or more other components of system 100. Portable or embedded device 102b may be configured to transmit data and information to other components of system 100, for example, via input network 104.

Portable or embedded device 102b may connect to input network 104 or one or more other components of system 100 by a wireless connection and/or a wired connection. In some embodiments, a wireless connection includes a WI-FI communication connection, a BLUETOOTH communication connection, a LI-FI communication connection, a NEAR FIELD COMMUNICATION (NFC) connection, and/or an optical wireless communication connection. In some embodiments, a wired connection includes a UNIVERSAL SERIAL BUS (USB) connection, a FIREWIRE connection, an ethernet connection, and/or a cable connection.

Personal wearable device 102c may be, for example, a fitness-tracking device, a smart watch, a wearable device, an implantable device, an electronic-textile device, an insulin-monitoring device, a blood-pressure-monitoring device, a heart-monitoring device, a moisture-detecting device, or a device configured to perform operations.

Personal wearable device 102c may be associated with a particular subject and may be wearable on the body or implanted in the body of the subject. Personal wearable device 102c may include a programmatic interface. A programmatic interface may allow the subject to interact using an alternate device. Personal wearable device 102c may comprise one or more sensors. Personal wearable device 102c may include hardware, software, and/or firmware. Personal wearable device 102c may include one or more memory units for storing instructions and one or more processors for executing the instructions to perform operations.

Personal wearable device 102c may be configured to detect and/or automatically connect to another device, such as personal device 102a, portable or embedded device 102b, invisible device 102d, administration device 102e, extended network device 102f, or any other connected device 102n. Personal wearable device 102c may connect to input network 104, as depicted in FIG. 1, or directly connect to lab bench manager 116 or one or more other components of system 100. Personal wearable device 102c may be configured to transmit data and information to other components of system 100, for example, via input network 104.

Personal wearable device 102c may connect to input network 104 or one or more other components of system 100 by a wireless connection and/or a wired connection. In some embodiments, a wireless connection includes a WI-FI communication connection, a BLUETOOTH communication connection, a LI-FI communication connection, a NEAR FIELD COMMUNICATION (NFC) connection, and/or an optical wireless communication connection. In some embodiments, a wired connection includes a UNIVERSAL SERIAL BUS (USB) connection, a FIREWIRE connection, an ethernet connection, and/or a cable connection.

Invisible device 102d may be comprise a sensor, for example, in a home, a wall, a ceiling, a floor, a socket, a light, an appliance such as a refrigerator or an oven, a furniture item such as a bed or a chair, a sink, a tap, a toilet, a workplace, a business, an office, a retail store, a school, a community center, a public space, an indoor space, an outdoor space, or a vehicle. Invisible device 102d may serve as a gateway or a pass-through of data or information from an external device (not shown in FIG. 1) to one or more other components of system 100.

Invisible device 102d may be associated with and/or provide data for multiple subjects. Invisible device 102c may include a programmatic interface. A programmatic interface may allow the subject to interact using an alternate device. Invisible device 102d may include one or more sensors configured to receive physiological data, environmental data, audio data, noise data, light data, motion data, temperature data, air quality data, water flow data, water quality data, and/or other data.

Invisible device 102d may include hardware, software, and/or firmware. Invisible device 102d may include one or more memory units for storing instructions and one or more processors for executing the instructions to perform operations.

Invisible device 102d may be configured to detect and/or automatically connect to another device, such as personal device 102a, portable or embedded device 102b, personal wearable device 102c, administration device 102e, extended network device 102f, or any other connected device 102n. IoT invisible device 102d may connect to input network 104, as depicted in FIG. 1, or directly connect to lab bench manager 116 or one or more other components of system 100. Invisible device 102d may be configured to transmit data and information to other components of system 100, for example, via input network 104.

Invisible device 102d may connect to input network 104 or one or more other components of system 100 by a wireless connection and/or a wired connection. In some embodiments, a wireless connection includes a WI-FI communication connection, a BLUETOOTH communication connection, a LI-FI communication connection, a NEAR FIELD COMMUNICATION (NFC) connection, and/or an optical wireless communication connection. In some embodiments, a wired connection includes a UNIVERSAL SERIAL BUS (USB) connection, a FIREWIRE connection, an ethernet connection, and/or a cable connection.

Administration device 102e is a device configured to perform operations. In some embodiments, administration device 102e includes a device configured to administer or deliver a drug. For example, administration device 102e may include an insulin-injecting device, an intravenous delivery device, or a wearable patch configured to administer or deliver a drug. In some embodiments, personal device 102a and administration device 102e are integrated as a single device.

Administration device 102e may include hardware, software, and/or firmware. Administration device 102e may include one or more memory units for storing instructions and one or more processors for executing the instructions to perform operations.

Administration device 102e may be configured to detect and/or automatically connect to another device, such as personal device 102a, portable or embedded device 102b, personal wearable device 102c, invisible device 102d, extended network device 102f, or any other connected device 102n. Administration device 102e may connect to input network 104, as depicted in FIG. 1, or directly connect to lab bench manager 116 or one or more other components of system 100. Administration device 102e may be configured to transmit data and information (e.g., confirmation of dosage administered, data regarding patient response to administration, etc.) to other components of system 100, for example, via input network 104.

Administration device 102e may connect to input network 104 or one or more other components of system 100 by a wireless connection and/or a wired connection. In some embodiments, a wireless connection includes a WI-FI communication connection, a BLUETOOTH communication connection, a LI-FI communication connection, a NEAR FIELD COMMUNICATION (NFC) connection, and/or an optical wireless communication connection. In some embodiments, a wired connection includes a UNIVERSAL SERIAL BUS (USB) connection, a FIREWIRE connection, an ethernet connection, and/or a cable connection.

Extended network device 102f is a device configured to provide data. Extended network device 102f may comprise stored data for multiple individuals. Extendable network device 102f may include a programmatic interface. A programmatic interface may allow the subject to interact using an alternate device. Extended network device 102f may include no sensors and may be solely a repository for stored or inputted data. Extended network device 102*f* may be connected to a sensor network, e.g., to receive and store data from a sensor network. Extended network device 102*f* may comprise electronic health records or other stored data.

Extended network device 102*f* may include hardware, software, and/or firmware. Extended network device 102*f* may include one or more memory units for storing instructions and one or more processors for executing the instructions to perform operations.

Extended network device 102*f* may be configured to detect and/or automatically connect to another device, such as personal device 102*a*, portable or embedded device 102*b*, personal wearable device 102*c*, invisible device 102*d*, administration device 102*e*, extended network device 102*f*, or any other connected device 102*n*. Extended network device 102*f* may connect to input network 104, as depicted in FIG. 1, or directly connect to lab bench manager 116 or one or more other components of system 100. Extended network device 102*f* may be configured to transmit data and information to other components of system 100, for example, via input network 104.

Extended network device 102*f* may connect to input network 104 or one or more other components of system 100 by a wireless connection and/or a wired connection. In some embodiments, a wireless connection includes a WI-FI communication connection, a BLUETOOTH communication connection, a LI-FI communication connection, a NEAR FIELD COMMUNICATION (NFC) connection, and/or an optical wireless communication connection. In some embodiments, a wired connection includes a UNIVERSAL SERIAL BUS (USB) connection, a FIREWIRE connection, an ethernet connection, and/or a cable connection.

Connected device 102*n* may include, for example, a personal computer, a server, a server cluster, a database, or a system configured to perform operations. In some embodiments, connected device 102*n* includes a health care provider system, a researcher system, a pharmacy system, a health insurance system, a medical system, an educational system, a financial system, and/or a government system. In some embodiments, connected device 102*n* includes a device, such as a device configured to administer or deliver a drug. For example, connected device 102*n* may include an insulin-injecting device, an intravenous delivery device, or a wearable patch configured to administer or deliver a drug.

In some embodiments, connected device 102*n* may include a programmatic interface. A programmatic interface may allow the subject to interact using an alternate device. In some embodiments, connected device 102*n* is hosted on a cloud. In some embodiments, connected device 102*n* is configured to retrieve data from a local or remote data storage (e.g., a drive, a database, a cloud storage) and/or transmit data to one or more other components of system 100.

Connected device 102*n* may include one or more sensors and may be connected to one or more sensor networks. In some embodiments, connected device 102*n* is configured to receive physiological data, environmental data, audio data, noise data, light data, motion data, temperature data, air quality data, water flow data, water quality data, and/or other data.

Connected device 102*n* may include hardware, software, and/or firmware. Connected device 102*n* may include one or more memory units for storing instructions and one or more processors for executing the instructions to perform operations.

Connected device 102*n* may be configured to detect and/or automatically connect to another device, such as personal device 102*a*, portable or embedded device 102*b*, personal wearable device 102*c*, invisible device 102*d*, administration device 102*e*, or extended network device 102*f*. Connected device 102*n* may connect to input network 104, as depicted in FIG. 1, or directly connect to lab bench manager 116 or one or more other components of system 100. Connected device 102*n* may be configured to transmit data and information to other components of system 100, for example, via input network 104.

Connected device 102*n* may connect to input network 104 or one or more other components of system 100 by a wireless connection and/or a wired connection. In some embodiments, a wireless connection includes a WI-FI communication connection, a BLUETOOTH communication connection, a LI-FI communication connection, a NEAR FIELD COMMUNICATION (NFC) connection, and/or an optical wireless communication connection. In some embodiments, a wired connection includes a UNIVERSAL SERIAL BUS (USB) connection, a FIREWIRE connection, an ethernet connection, and/or a cable connection.

Input data storage 106, template storage 108, configured bench storage 110, and/or processed data storage 112 may include, for example, data stored in a database. Input data storage 106, template storage 108, configured bench storage 110, and/or processed data storage 112 may be located on the same or different computers, drives, devices, databases, servers, server clusters, buckets, and/or cloud services.

Input data storage 106, template storage 108, configured bench storage 110, and/or processed data storage 112 may connect to bench network 114, as depicted in FIG. 1, or directly connect to lab bench manager 116 or one or more other components of system 100.

Input data storage 106, template storage 108, configured bench storage 110, and/or processed data storage 112 may be secure storage, for example, requiring a secure connection and authentication for access. Input data storage 106, template storage 108, configured bench storage 110, and/or processed data storage 112 may include encrypted data and/or be configured to receive and/or transmit data using one or more methods of encryption.

Input data storage 106 may include, for example, data from one or more devices such as personal device 102*a*. In some embodiments, input data storage 106 includes sensor data, subject-device data, subject-reported data, contextual relational data, marker reported data, social-media data, crowd-sourced data, traditional media and telecom reported data, health data, instrument data, IoT data, laboratory data, urine data, blood data, imaging data, provider data, and/or lab-results data.

Input data storage 106 may be configured to receive an upload of data and/or a continuous stream of data. The upload may be instantaneous or momentary. Input data storage 106 may include data that is associated with data collection parameters. In some embodiments, a data collection parameter may include a frequency of data collection, a duty cycle or collection timing, a publishing schedule or interval, a QoS number of times that data were collected or reported in a given scenario (e.g., duplicate, triplicate, maximum limit reached for the day), and/or a configuration or control to a hardware or software setting.

Input data storage 106 may include data that may belong to one or more variable classes. For example, input data storage 106 may include heart-rate data that belongs to a heart variable class and a sleep variable class based on, for example, a contention that heart rate indicates whether an individual is awake or asleep.

Template storage 108 may include, for example, data associated with a workbook template, a marker template, and/or a therapeutic recipe template. Template storage 108 may include expressions (e.g., rules, formulas, algorithms, models) for processing data. For example, template storage 108 may include a rule that involves calculating averages, calculating medians, smoothing data, normalizing data, filtering data, sampling data, weighting data, combining data, and/or comparing data. In some embodiments, template storage 108 includes a rule for generating a score (e.g., a predictor score, an outcome score, a marker score, a therapy adherence score) from data. In some embodiments, template storage 108 includes a rule for generating a metric (e.g., a marker metric, a therapy impact metric) from data.

Configured bench storage 110 may include, for example, data associated with a workbook template, a marker template, and/or a therapeutic recipe template. Configured bench storage 110 may include expressions (e.g., rules, formulas, algorithms, models) for processing data. For example, configured bench storage 110 may include a rule that involves calculating averages, calculating medians, smoothing data, normalizing data, filtering data, sampling data, weighting data, combining data, and/or comparing data. In some embodiments, configured bench storage 110 includes a rule for generating a score (e.g., a predictor score, an outcome score, a marker score, a therapy adherence score) from data. In some embodiments, configured bench storage 110 includes a rule for generating a metric (e.g., a marker metric, a therapy impact metric) from data.

Processed data storage 112 may include, for example, an output, a score (e.g., a predictor score, an outcome score, a marker score, a therapy adherence score), a metric (e.g., a marker metric, a therapy impact metric), a report, and/or a result.

Lab bench manger 116 may include hardware, software, and/or firmware. Lab bench manger 116 may include one or more memory units for storing instructions and one or more processors for executing the instructions to perform operations. In some embodiments, lab bench manager 116 may include a personal computer, a server, a server cluster, and/or a cloud service. Lab bench manger 116 may include data storage. For example, lab bench manager 116 may include input data storage 106, template storage 108, configured bench storage 110, and/or processed data storage 112.

One or more components of system 100 may connect to input network 104 and/or bench network 114. In some embodiments, input network 104 connects devices 102a-102n and facilitates the transmission of data to and from the components connected by bench network 114. In some embodiments, bench network 114 connects components related to the storage, analysis, manipulation, and reporting of data. Although input network 104 connects devices that generally input data, data may flow in either direction (e.g., to or from devices 102a-102n). Data may flow in either direction in bench network 114. In some embodiments, input network 104 includes bench network 114. In some embodiments, bench network 114 includes network 104. In some embodiments, input network 104 and bench network 114 are a single network.

Input network 104 may be a public network or a private network and may include, for example, a wired network or a wireless network. In some embodiments, input network 104 may be a local area network (LAN), a wide area network (WAN), a metropolitan area network (MAN), an IEEE 802.11 wireless network, a WI-FI network, a network of networks, the Internet, and/or a land-line telephone network. In some embodiments, input network 104 may be a secure network, for example, requiring a password or authentication for access.

Bench network 114 may be a public network or a private network and may include, for example, a wired network or a wireless network. In some embodiments, bench network 114 may be a local area network (LAN), a wide area network (WAN), a metropolitan area network (MAN), an IEEE 802.11 wireless network, a WI-FI network, a network of networks, the Internet, and/or a land-line telephone network. In some embodiments, bench network 114 may be a secure network, for example, requiring a password or authentication for access.

Figure 2:
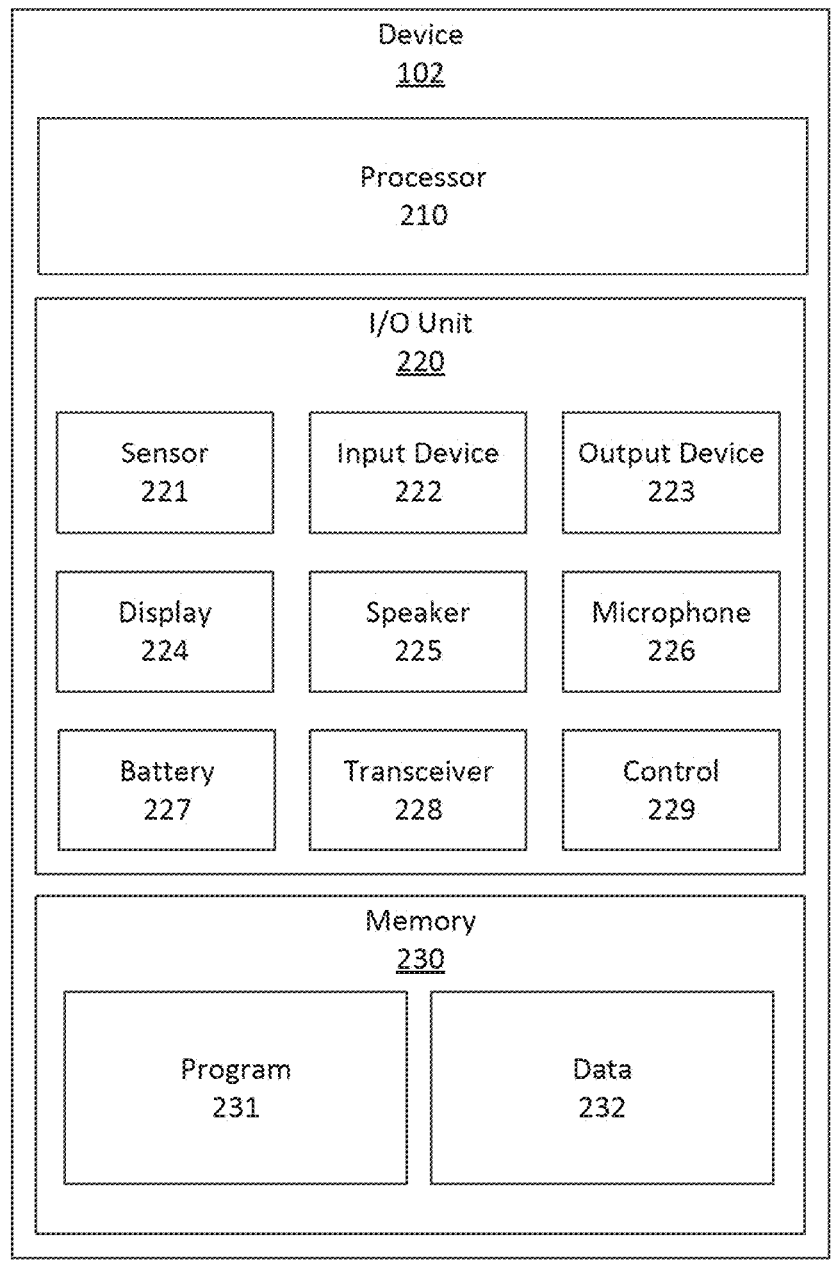
FIG. 2 is a diagram of an exemplary device, consistent with disclosed embodiments.

FIG. 2 is a diagram of an exemplary device 102, consistent with disclosed embodiments. Device 102 may be, for example, personal device 102a, portable or embedded device 102b, personal wearable device 102c, invisible device 102d, administration device 102e, extended network device 102f, and/or connected device 102n.

Device 102 may include one or more components. Device 102 may include, for example, a processor 210, an input/output (I/O) unit 220, and a memory 230. Device 102 may include one or more of each component, it may include only some of these components, and it may include other components not depicted in FIG. 2. Components of device 102 may be arranged in various ways.

Processor 210 may be, for example, a computing processor. In some embodiments, processor 210 is a microprocessor. Processor 210 may be, for example, a single-core processor or a multiple-core processor (e.g., dual core, quad core). In some embodiments, processor 210 includes a single-core processor configured with virtual processing technologies. In some embodiments, processor 210 includes logical processors to simultaneously execute and control multiple processes. Processor 210 may implement technologies such as virtual-machine technologies to execute, control, run, manipulate, and/or store multiple processes, applications, and/or programs. In some embodiments, processor 210 includes a multiple-core processor configured to provide parallel processing functionalities for execution of multiple processes simultaneously. Processor 210 may be configured, for example, to execute one or more instructions stored in memory 230 to perform operations.

I/O unit 220 may include, for example, sensor 221, input device 222, output device 223, display 224, speaker 225, microphone 226, battery 227, transceiver 228, and/or a mechanical control such as control 229. In some embodiments, I/O unit 220 is part of device 102. In some embodiments, I/O unit 220 is part of a different device that is connected to device 102.

Sensor 221 may include, for example, a location or positioning sensor (e.g., a GPS sensor), a relative location or positioning sensor (e.g., a received signal strength indicator from a wireless access point, cellular tower, a portable nearby sensor), a magnetic field sensor (e.g., a magnetometer), a light sensor (e.g., an ambient light sensor), an audio sensor (e.g., an ambient noise sensor), an orientation sensor (e.g., a gyroscope), a movement or motion sensor (e.g., an accelerometer, a light-based motion detector), a personal identification sensor (e.g., a fingerprint detector, an iris scanner, a face detection scanner), a moisture sensor (e.g., a humidity sensor), temperature sensor (e.g., a body temperature sensor, a skin temperature sensor, a room temperature sensor), an electrocardiography sensor (e.g., an ECG, an R-R interval detector, a heart rate monitor), an electroencephalography sensor (e.g., an EEG), a photoplethysmography sensor (e.g., a pulse rate monitor, a pulse oximeter), an electrodermal sensor (e.g., a galvanometer), an auscultation sensor (e.g., a stethoscope, a blood pressure monitor), a blood-chemistry sensor (e.g., a glucose monitoring sensor, a ketone monitoring sensor), a load sensor (e.g., a weight scale sensor), a barometric pressure sensor (e.g. a barometer, an altimeter), a wave-detection sensor (e.g., a lidar sensor, a radar sensor, a sonar sensor), a gas sensor (e.g., a chromatography sensor, a smoke detector, an alcohol sensor, a dust particle sensor), and/or a water sensor (e.g., a chemical sensor, a turbidity sensor, a flow meter).

Input device 222 may include, for example, a touchpad, a touch screen, a keyboard, a mouse, a button, a dial, a knob, a switch, a microphone, a camera, a video camera, a fingerprint scanner, an eye scanner, near field communication sensor, an RFID tag scanner, a smart card reader, and/or an ultrasonic scanner.

Output device 223 may include, for example, a visual display (e.g., display 224), a light (e.g., a frequency or color-controlled light), a speaker (e.g., speaker 225), a mechanical control line, an electrical control line, a software control line, a radio control band (e.g., ISM, WIFI, BLUETOOTH), a broadcast radio band (e.g., emergency broadcast, FM, VHF, UHF, and/or a haptic feedback device (e.g., a vibration motor).

Display 224 may include, for example, a light-emitting display (e.g., a light emitting diode (LED) display, a lamp), a liquid-crystal display (LCD), a touch screen, and/or a projector.

Speaker 225 may include, for example, a wired speaker and/or a wireless speaker.

Microphone 226 may include, for example, a wired headset, a wired microphone, a wireless headset, and/or a wireless microphone.

Battery 227 may include, for example, a lithium-ion battery, a lithium battery, a large capacitor, a silver-oxide battery, a lead-acid battery, an alkaline battery, a zinc-air battery, and/or a nickel-cadmium battery. In some embodiments, battery 227 is a rechargeable battery. In some embodiments, battery 227 is a disposable battery. In some embodiments, battery 227 is configured to provide approximately constant voltage (e.g., 3 volts, 9 volts, 12 volts) to device 102.

In some embodiments, battery 227 may have a battery life that changes based on operations performed by device 102 and/or based on device settings of device 102. In some embodiments, the battery life of battery 227 may be extended if, for example, processor 210 performs fewer operations, memory 230 management needs are reduced, or I/O unit 220 demands are reduced. In some embodiments, the processor, memory, and I/O units do not affect each other directly. In some embodiments, the battery life of battery 227 may be shortened if, for example, processor 210 performs more operations, memory 230 management needs increase, or I/O unit 220 demands increase. In some embodiments, the battery life of battery 227 may be extended by placing device 102, processor 210, I/O unit 220, and/or memory 230 in a sleep mode. In some embodiments, the battery life of battery 227 may be shortened or extended by adjusting I/O unit 220, sensor 221 (e.g., enabling or disabling, or by adjusting a frequency and/or a type of data collection), input device 222 (e.g., disabling specific interrupts when multiple conditions do not exist, such as not processing a volume down action when a volume is at 0 or off), output device 223 (e.g., disabling a cellular radio or WIFI from synchronizing with a server when new sensor data 221 does not exist), display 224 (e.g., by adjusting a display brightness, or the responsiveness to enable or disable when a subject is present versus absent), speaker 225 (e.g., by adjusting a loudness, by disabling the audio amplifier circuit when the volume is reduced to 0 or off), and/or transceiver 228 (e.g., by adjusting bandwidth usage, by disabling a radio to reduce interrupts that drive memory 230 and processor usage 210).

Transceiver 228 may include, for example, a WI-FI transceiver, a LI-FI transceiver, a Near Field Communication (NFC) transceiver, a radio transceiver, an ultra-high frequency (UHF) transceiver, a BLUETOOTH transceiver, an infrared transceiver, and/or a transceiver configured to connect with a cellular data network. In some embodiments, transceiver 228 may be configured to receive and/or transmit data according to a limited bandwidth (e.g., via channel).

Control 229 may include a device for performing operations, for example, a patch, a direct-injection device (e.g., a syringe), and/or a device configured to administer or deliver a drug. In some embodiments, control 229 is an insulin-dispensing device. In some embodiments, control 229 includes a device that adjusts the flow of a drug. In some embodiments, control 229 includes a prescription-fulfilling device, a pill dispenser, a bottler, and/or a labeling device.

Memory 230 may include, for example, volatile memory, non-volatile memory, magnetic memory, semiconductor memory, optical memory, removable memory, and/or non-removable memory. Memory 230 may include, for example, storage and/or non-transitory tangible computer-readable media. In some embodiments, memory 230 includes software that can be integrated into a computer system, non-transitory tangible computer-readable media, and/or existing communications software. In some embodiments, memory 230 includes an operating system for performing operations when executed by one or more processors.

In some embodiments, memory 230 includes a program (e.g., program 231). The program may include, for example, modules, codes, scripts, and/or algorithms. In some embodiments, a program is written in one or more programming languages and/or scripting languages. In some embodiments, a program may be implemented and/or replicated as firmware or circuit logic. In some embodiments, a program collects data via I/O unit 220. Some embodiments may use a type of memory that can have a larger or lesser drain on battery and processor for continued upkeep and refresh cycles within the circuit design. Some embodiments may use a type of memory that has an extended or limited number of reads or writes until memory failure occurs and power demand is impacted. In some embodiments, a program transmits data over a network and/or a direct connection, authenticates a subject, creates and/or edits a subject profile, records and/or analyzes voice data, captures image data, records and/or analyzes video data, detects finger prints, receives and/or transmits data, displays or plays a message, generates haptic feedback, and/or stores data.

In some embodiments, memory 230 includes data (e.g., data 232). In some embodiments, data may be encrypted and/or unencrypted. In some embodiments, data is collected using I/O unit 220. In some embodiments, data includes metadata and/or device data (e.g., one or more device settings). In some embodiments, data includes one or more databases comprising an organized or structured collection of tables, queries, objects, schema, reports, and/or views.

Figure 3:
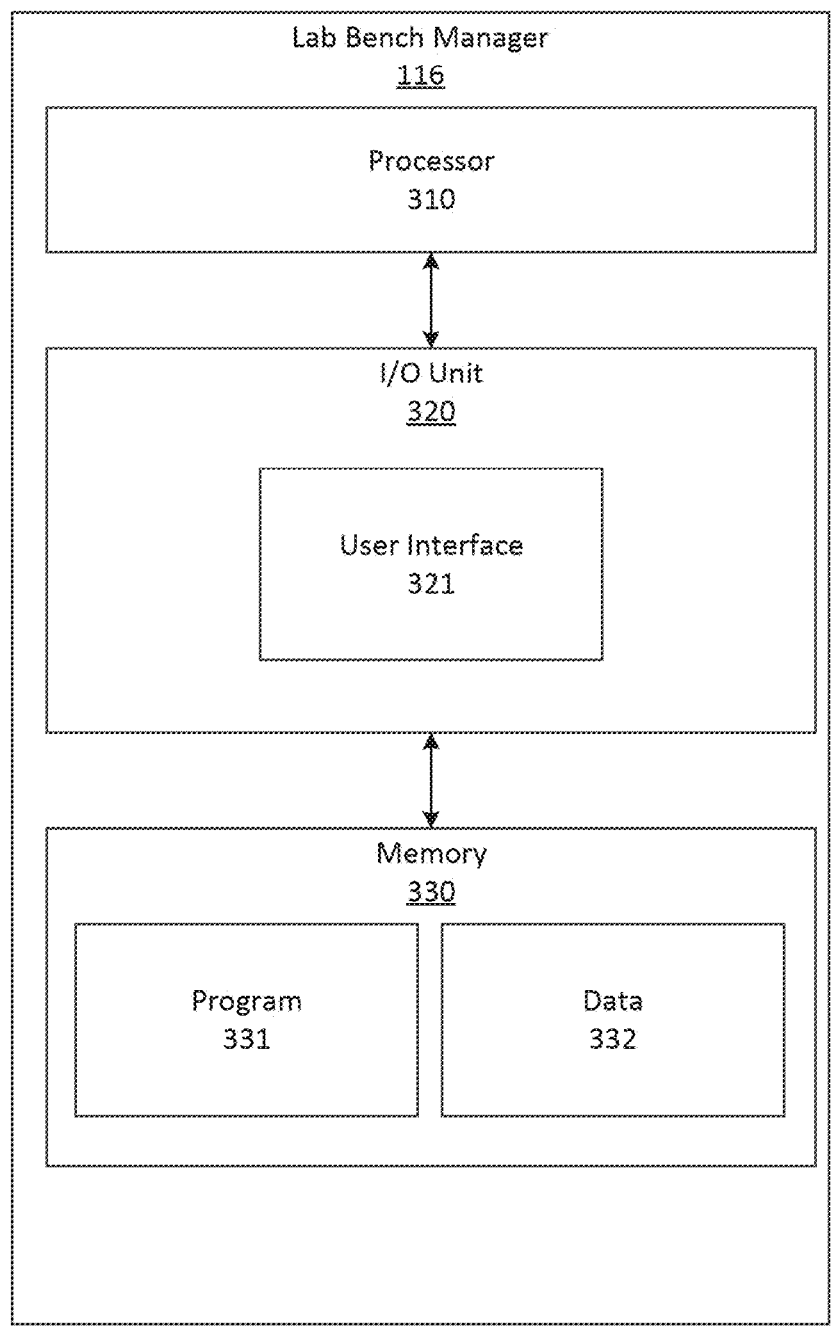
FIG. 3 is a diagram of an exemplary lab bench manager, consistent with disclosed embodiments.

FIG. 3 is a diagram of an exemplary lab bench manager 116, consistent with disclosed embodiments. Lab bench manager 116 may include one or more components. Lab bench manager 116 may include, for example, a processor 310, an I/O unit 320, and a memory 330. Lab bench manager 116 may include one or more of each component, it may include only some of these components, and it may include other components not depicted in FIG. 3. Components of lab bench manager 116 may be arranged in various ways.

Processor 310 may be, for example, a computing processor. In some embodiments, processor 310 is a microprocessor. Processor 310 may be, for example, a single-core processor or a multiple-core processor (e.g., dual core, quad core). In some embodiments, processor 310 includes a single-core processor configured with virtual processing technologies. In some embodiments, processor 310 includes logical processors to simultaneously execute and control multiple processes. Processor 310 may implement technologies such as virtual-machine technologies to execute, control, run, manipulate, and/or store multiple processes, applications, and/or programs. In some embodiments, processor 310 includes a multiple-core processor configured to provide parallel processing functionalities for execution of multiple processes simultaneously. Processor 310 may be configured, for example, to execute one or more instructions stored in memory 330 to perform operations.

I/O unit 320 may include, for example, a user interface 321. In some embodiments, I/O unit 320 is part of lab bench manager 116. In some embodiments, I/O unit 320 is part of a separate device that is connected to lab bench manager 116. In some embodiments, I/O unit 320 includes one or more components connected to input network 104 and/or bench network 114. In some embodiments, I/O unit 320 receives data from and/or transmits data to one or more components of system 100.

User interface 321 may include, for example, a display, an LED, a touchscreen, a keyboard, a microphone, a speaker, a haptic device, a camera, a button, a dial, a switch, a knob, an input device, and/or an output device. In some embodiments, user interface 321 includes components for receiving inputs and/or generating and displaying a workbook. In some embodiments, user interface 321 may include a display capable of managing and/or displaying one or more menus and/or workbooks (e.g., a user interface as depicted in FIG. 4, FIG. 5, FIG. 6, or FIG. 7).

Memory 330 may include, for example, volatile memory, non-volatile memory, magnetic memory, semiconductor memory, optical memory, removable memory, and/or non-removable memory. Memory 330 may include, for example, storage and/or non-transitory tangible computer-readable media. In some embodiments, memory 330 includes software that can be integrated into a computer system, non-transitory tangible computer-readable media, and/or existing communications software. In some embodiments, memory 330 includes an operating system for performing operations when executed by one or more processors.

In some embodiments, memory 330 includes a program (e.g., program 331). The program may include, for example, modules, codes, scripts, and/or algorithms. In some embodiments, a program is written in one or more programming languages and/or scripting languages. In some embodiments, a program may be implemented and/or replicated as firmware or circuit logic. In some embodiments, a program collects data via I/O unit 320. In some embodiments, a program transmits data over a network and/or a direct connection, authenticates a user, creates and/or edits a user profile, records and/or analyzes data, receives and/or transmits data, displays or plays a message, and/or stores data.

In some embodiments, memory 330 includes data (e.g., data 332). In some embodiments, data may be encrypted and/or unencrypted. In some embodiments, data is collected using I/O unit 320. In some embodiments, data includes metadata and/or lab bench manager data (e.g., one or more settings). In some embodiments, data includes one or more databases comprising an organized or structured collection of tables, queries, objects, schema, reports, and/or views.

Figure 4:
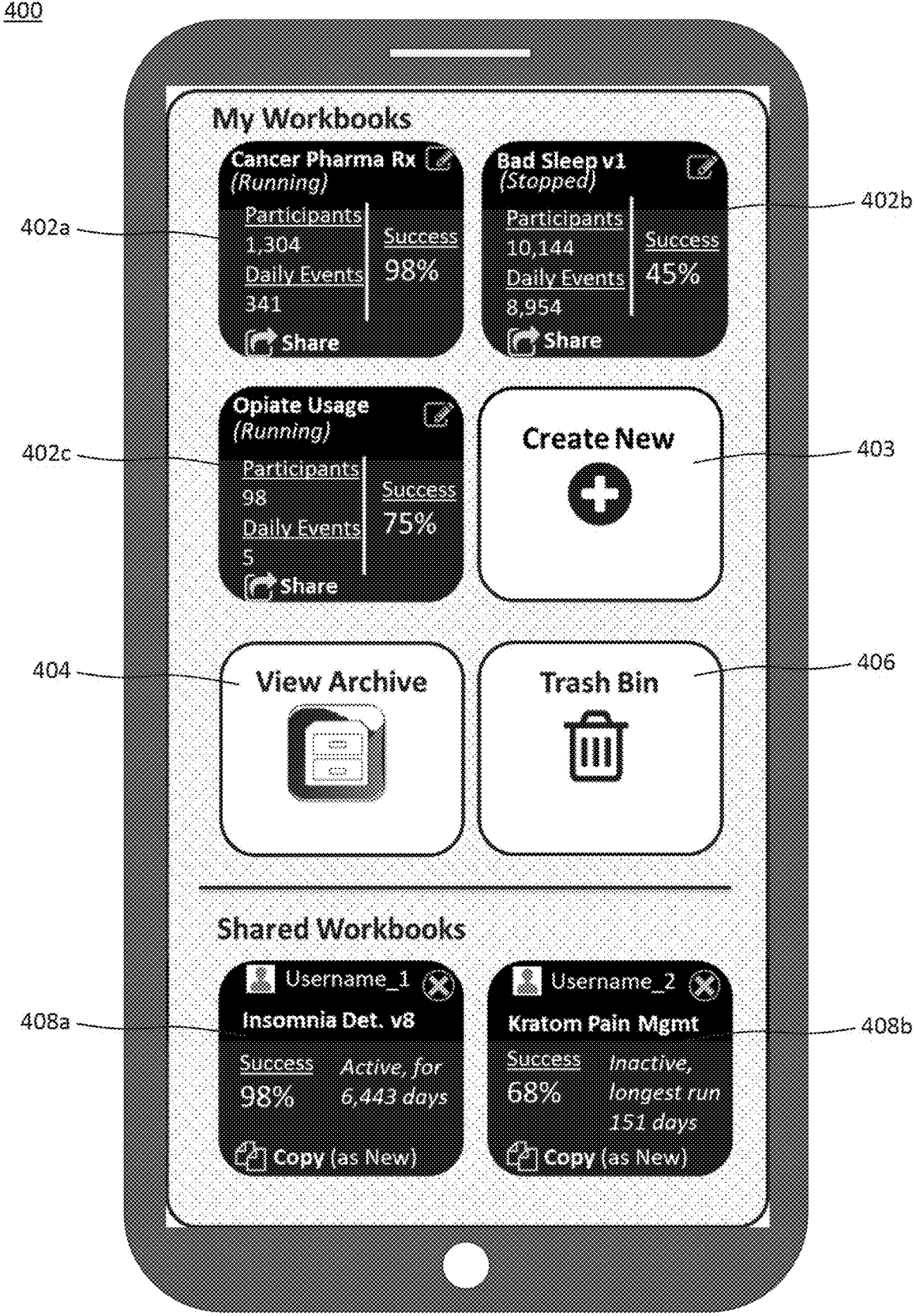
FIG. 4 is a diagram of an exemplary lab bench manager interface, consistent with disclosed embodiments.

FIG. 4 is a diagram of an exemplary lab bench manager interface 400, consistent with disclosed embodiments. Consistent with the disclosure, implementations of lab bench manager interface 400 may involve the same or different icons, information within icons, available functions, and/or other features.

Lab bench manager interface 400 is shown in FIG. 4 as displayed by a smart phone using a mobile browser. Lab bench manager interface 400 may provide a dashboard-style interface that is divided into a "My Workbooks" section and a "Shared Workbooks" section.

The My Workbooks section may contain one or more icons related to workbooks created by a user. As shown in FIG. 4, the My Workbooks section may contain user workbook icons 402a, 402b, and 402c. Each user workbook icon 402 may display the workbook title, operating status, select reporting metrics, editing options, and/or sharing options for the user's workbook. For example, user workbook icon 402a provides a user with access to a workbook titled "Cancer Pharma Rx," which has a "running" operating status. A "running" operating status indicates the workbook is actively receiving data and/or generating output. The pencil-in-a-box icon in the upper right-hand corner of user workbook icon 402a indicates that the user can edit the workbook by selecting the pencil-in-a-box icon. The arrow-in-a-box icon in the lower left-hand corner of user workbook icon 402a indicates that the user has the ability to share the workbook (e.g., to provide reading and/or writing capabilities to another user) by selecting the arrow-in-a-box icon. The select reporting metrics displayed for the Cancer Pharma Rx workbook include the number of participants (1,304), the number of daily events (341), and the success rate (98%). Thus, for the "Cancer Pharma Rx" workbook, there are 1,304 participants that meet the qualifying criteria for applicability and collection. Of these 1,304 participants, there are 341 analyzed daily events. Of these 341 daily events, the current total success rate since the workbook was created is a 98% success in the marker accurately predicting the observed condition.

The My Workbooks section may contain one or more icons allowing a user to create a new workbook. As shown in FIG. 4, the My Workbooks section may contain a new workbook icon 403, which, when selected by the user, allows a user to develop a new workbook. Once created, the new workbook may then be represented by a new user workbook icon 402.

The My Workbooks section may contain one or more icons allowing a user to view archived workbooks. As shown in FIG. 4, the My Workbooks section may contain a view archive icon 404, which, when selected by the user, allows the user to view and/or manage (e.g., move, delete, edit) previously archived workbooks. By archiving certain workbooks, a user can manage the number of icons on the user interface, creating a more user-friendly interface for identifying the workbooks of particular interest to a user.

The My Workbooks section may contain one or more icons allowing a user to delete workbooks. As shown in FIG. 4, the My Workbooks section may contain a view trash icon 406, which, when selected by the user, allows the user to delete a workbook.

The Shared Workbooks section may contain one or more icons related to workbooks created by a second user (i.e., a user other than the user that created workbooks represented by icons in the My Workbooks section) and shared with the first user (i.e., the user that created the workbooks represented by icons in the My Workbooks section). For example, a second user may create a workbook and then grant reading or writing privileges to that workbook (e.g., share that workbook), with the first user. Icons representing those shared workbooks may be provided in the Shared Workbooks section of FIG. 4. Shared workbook icons 408a and 408b are shown in the Shared Workbooks section of FIG. 4. Each shared workbook icon 408 may display the workbook creator information, the workbook title, operating status, select reporting metrics, removal options, and copying options for creating a new workbook. For example, shared workbook icon 408a includes the workbook creator information of a small photo and "Username_1" for the workbook titled "Insomnia Det. v8," which has an "active" operating status. The operating status of "running" for a "My Workbook" workbook and "active" for a "Shared Workbook" workbook may generally indicate the same functional status (e.g., data is still being collected, the analysis is ongoing), but different word choices in the interface assist the user in recognizing which workbooks she created/owns and which ones are shared with her. A first user may "stop" an owned workbook, but a functionally similar status for a shared workbook may use the indicator "inactive." The select reporting metrics for shared workbook icon 408a include a number of days active (6,443) and a success rate (98%). The first user may remove shared workbook icon 408a from interface 400 by selecting, for example, the x-in-a-circle close box.

The ability to configure a shared workbook may be limited due to ownership of the given workbook and the read and/or write rights given by the creator or owner of the workbook. Thus, to make modifications, the first user may also create a new workbook based on a copy of the shared workbook by selecting the "Copy (as New)" option at the bottom of shared workbook icon 408a.

Selection of an icon may happen in any manner known to a person of ordinary skill in the art, e.g., tapping the icon or a portion of the icon using a touch-screen interface, clicking the icon or a portion of the icon using a mouse pointer, dragging one icon to another icon. The icons are also re-sortable as desired by the user, e.g., by dragging icons dynamically on the page to resort as preferred for viewing preferences, by requesting sorting based on name of workbook and/or type of icon.

Deletion and/or removal of an icon from lab bench manager interface 400 (e.g., dragging a user workbook 402 icon to the trash icon 406, selecting the close icon of a shared workbook icon 408) may result in at least one of removal of the icon from the interface 400, temporary deletion of the workbook (e.g., where the workbook resides in a "trash" file and, optionally, the workbook processes are stopped or inactivated), or permanent deletion.

Figure 5:
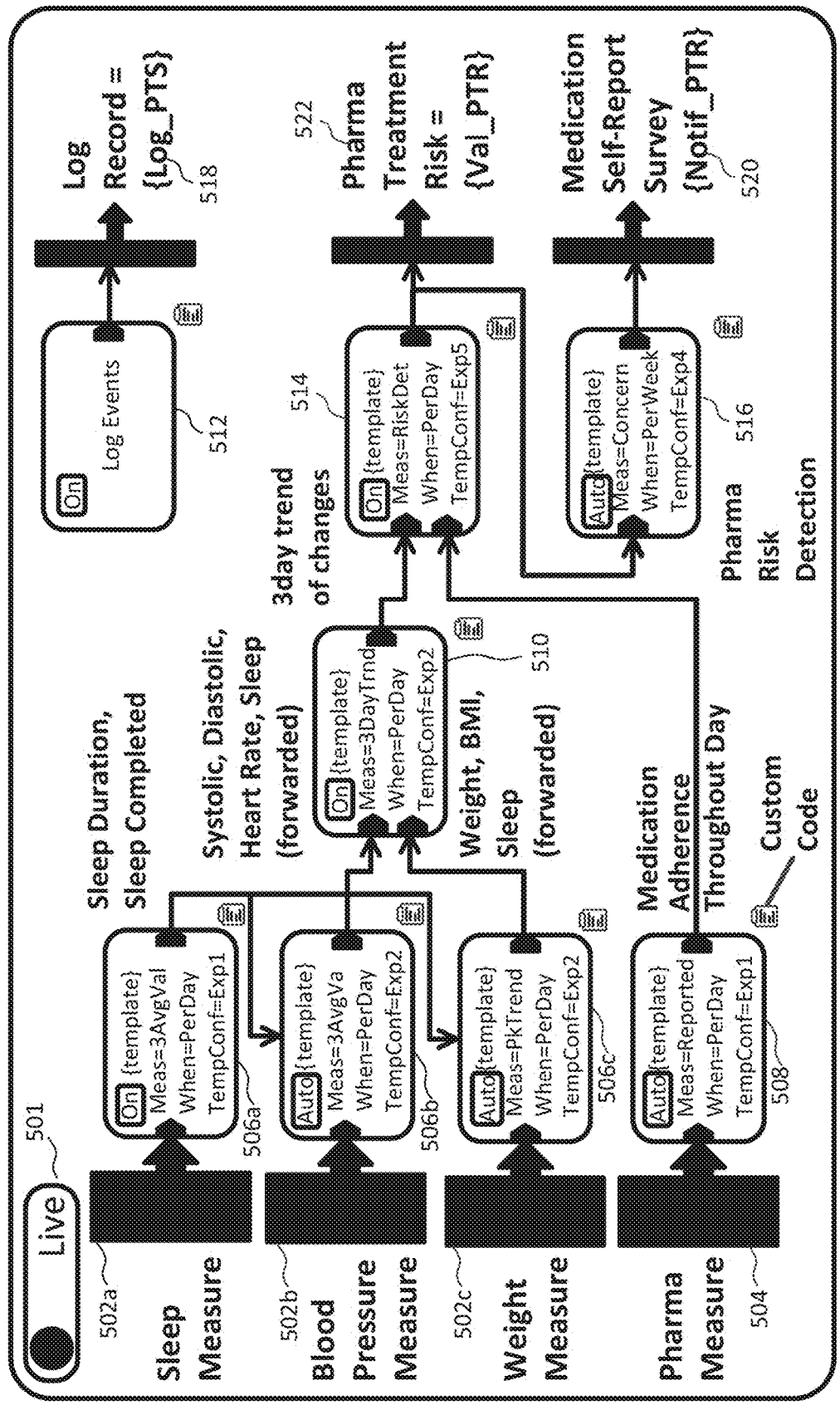
FIG. 5 is a diagram of an exemplary workbook interface, consistent with disclosed embodiments.

FIG. 5 is a diagram of an exemplary workbook interface 500 provided by lab bench manager 116, consistent with disclosed embodiments.

Consistent with the disclosure, implementations of workbook interface 500 may involve the same or different variable classes, rules, metrics, scores, or other features.

Workbook interface 500 provides an exemplary interface for a workbook intended to generate a marker that predicts whether a subject adheres to a therapy. Once generated, this marker may be used to compare self-reported medication adherence to under understand if subjects are taking their medication, potentially lying, or having other difficulties that may render the pharmaceutical measure inconclusive. That is, the outcome of interest may be the pharmaceutical measure of whether a medication is at therapeutic levels in a subject. The medication may be known to often affect patient's sleep, blood pressure, and weight, so the model may involve comparing the subject's sleep, blood pressure, and weight scores (e.g., predictor variables used to calculate a marker score) with the subject's self-reported medication adherence (e.g., an outcome score). A marker metric may be developed from the comparison, and a marker metric showing a close relationship between the marker score and the outcome score may indicate that the subject is taking their medication. A marker metric score showing a distant relationship may indicate that the subject is potentially lying (e.g., altering the outcome score) or that the marker is not a good predictor of the outcome (e.g., other variables should be considered in creating the marker).

As shown, workbook interface 500 provides the user the ability to use live, stored (e.g., pre-recorded) data, or a combination of live and stored data. Toggle switch 501 indicates the use of live data has been selected for this workbook.

Workbook interface 500 includes three predictor variable classes: sleep measure 502a, blood pressure measure 502b, and weight (bodyweight) measure 502c. Workbook interface 500 includes one outcome variable class: pharma measure 504. In the example of FIG. 5, a user may have selected the predictor and outcome variable classes based on a set of available variable classes and a model. For example, a user may have a model that sleep, blood pressure, and weight predict a pharmaceutical measure. An available variable class may mean that stored data is available for that variable class or that data for that variable class can be obtained (e.g., personal device 102a may be configured to begin collecting and/or transmitting the needed data).

Workbook interface 500 includes expressions 506a, 506b, 506c, 508, and 510. The expressions generate scores based on received data and one or more rules. The expressions may be custom expressions or template expressions (e.g., a set of predetermined expressions or partially customizable expressions may be available to the user). Expressions 506a, 506b, and 506c generate predictor scores. For example, expression 506a may generate a sleep duration score based on received motion data and a rule (e.g., a 3-day average). Expression 506b may generate a blood pressure score based on received systolic and diastolic pressure measurements, a heart rate measurement, and an averaging rule. As shown, the blood pressure score generated by expression 506b may be further based on the sleep score generated by expression 506a. Expression 506c may generate a weight score based on bodyweight data, sleep data, and an averaging rule.

Expression 508 generates an outcome score. For example, expression 508 may generate a medication adherence score based on self-reported data or other data. As explained above, the difference between a predictor score and an outcome score is its function in a model. A predictor score is used to develop and/or identify a marker, and an outcome score (e.g., the score representing the real-world data for the outcome of interest) can then be compared to the marker to determine the marker metric (e.g., how good of a fit the marker is for the outcome of interest). The specific data represented by a score may be used to calculate either a predictor score or an outcome score, depending on how the model is configured. For example, a medication adherence score may be a predictor score for a model that medication adherence and weight predict the risk of an adverse event, or it may be an outcome score for a model that sleep, blood pressure, and weight can predict medication adherence (e.g., that a patient is receiving a therapeutic amount of medicine).

Expression 510 may generate a marker score based on the sleep score (e.g. the result of applying expression 506*a*), blood pressure score (e.g., the result of applying expression 506*b*), weight score (e.g., the result of applying expression 506*c*), and a marker rule.

Workbook interface 500 may include a relationship expression 514, which generates a marker metric describing how well the marker predicts the outcome based on a relationship. In this example, the marker relationship is a relationship between the marker score of expression 510 and the medication adherence score of expression 508 (e.g., statistical relationship, a descriptive relationship, a model). For example, the relationship may be a linear regression between the marker score time series and the medication adherence score time series. The marker metric is an indicator of how well the marker relationship describes the observed data (e.g., a goodness of fit measure, a regression coefficient, an R-squared value, other metric). Application of relationship expression 514 may also result in generation of result report 522, which provides notification on the performance of the marker to the user.

As shown, workbook interface 500 may include reporting expressions to generate reports. The reports may include aggregated data (e.g., tables, figures, other data representations) and/or analysis results (e.g., confidence intervals, odds ratios, other analysis results). For example, reporting expression 516 may generate a medication self-report survey 520, which may request information from the subject, for example, when the result report 522 shows a specified level of risk. Survey 520 may comprise one or more questions for a subject to answer. In some embodiments, a delay or failure to answer one or more questions may also be considered a response to survey 520. In some embodiments, survey 520 is used to understand whether a subject is taking or has taken her medication, is potentially lying, or is having difficulties that may render result report 522 inconclusive.

Workbook interface 500 may include log function 512 that logs (e.g., records) changes to the workbook configuration, session data (e.g., user access times, download events), and metadata associated with received data (e.g., connected devices, timestamps, device settings). The log may be accessible to the user in the form of, for example, log record 518.

Figure 6:
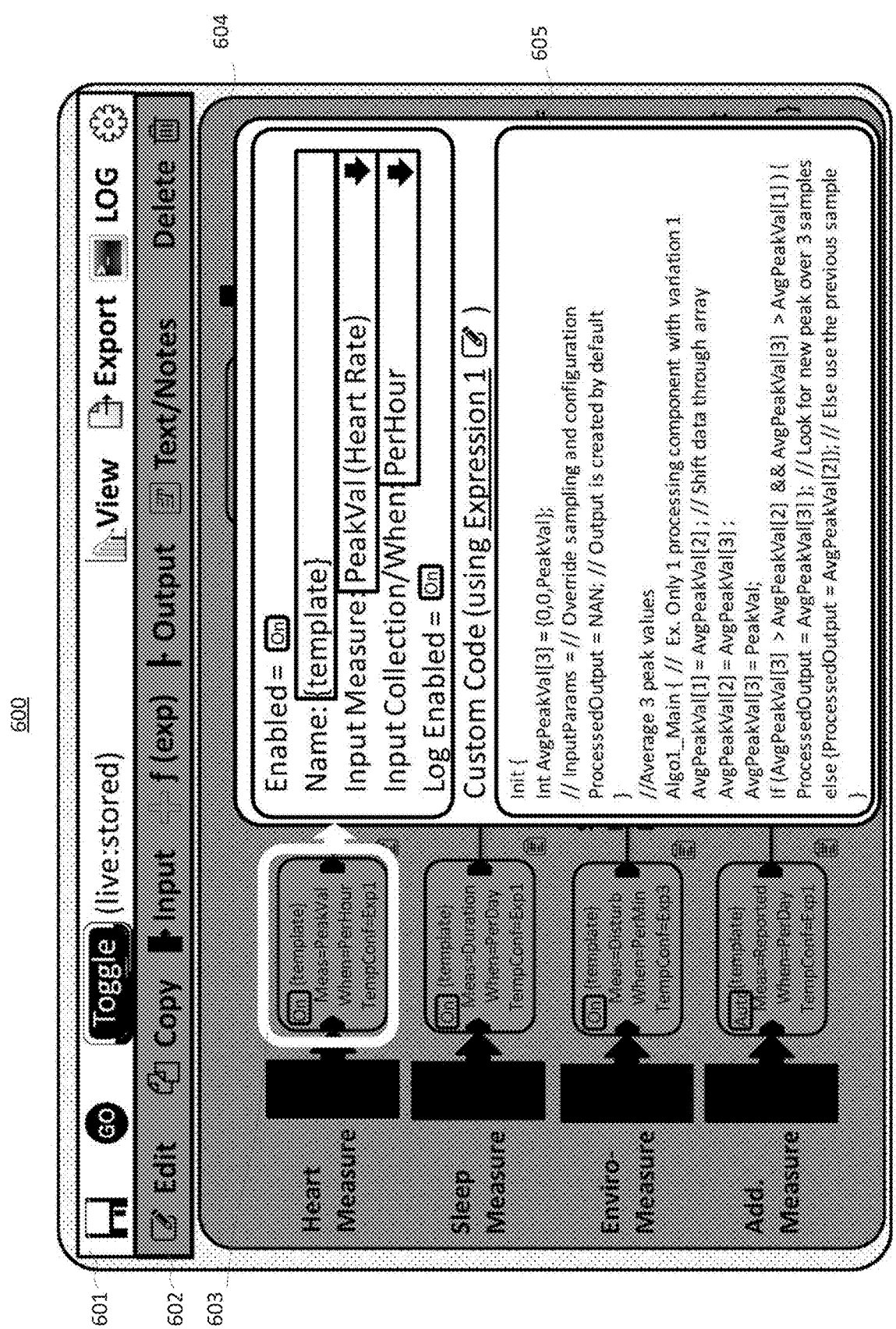
FIG. 6 is a diagram of an exemplary workbook interface, consistent with disclosed embodiments.

FIG. 6 is a diagram of an exemplary workbook interface 600 provided by lab bench manager 116, consistent with disclosed embodiments.

At the top row 601 of the interface, workbook interface 600 provides options to save changes (the floppy disc icon), execute the changes (the "GO" icon), toggle the workbook data usage from live data to stored data (the "Toggle" icon), view a report of the processed data (the "View" icon), export the data (the "Export" icon), view a real-time monitoring log of one or more expressions and/or data (the "LOG" icon), and adjust the overall settings of the workbook (the gear icon). The icons and their related options presented in top row 601 do not constrain the disclosure. For example, the "Toggle" icon may be configured to allow the use of live data, stored data, or a combination of live and stored data. Furthermore, the term "live data" may be an indicator that there are controls available to modify the collection of the data.

The settings for a workbook may include uploading a test data file for use by the workbook. The test data file may provide a set of data to be used by the workbook instead of or in addition to other data available to the workbook (e.g., instead of or in addition to the live or stored data). In some embodiments, a user is able to reference data similar to data received from an input data storage or a template storage as additional arrays of data to replace or augment the available analysis configured in the lab bench.

The settings for a workbook may include a range setting for data, which may indicate how long the workbook should remain active and/or what range of stored data should be used by the workbook. Such range may be a global range for stored, test, live data selection, or a combination thereof. When selecting a specific range within a given source, a range setting may, for example, describe a start date of today with a specific end date or no end date (e.g., indicating the collection of live data), a specific pre-existing range (e.g., indicating the use of stored data), or a combination of these options. The system may be configured to indicate if data is unavailable on a given date. In some embodiments, specified data may not have a data range associated with it, for example, in the case of factors and algorithmic tables that may contain baselined data. In some case, the data range specified may be a number of data points from 1 to n and give an option to pick a start ID of data or an ending ID of data.

The settings for a workbook may include subject selection criteria for filtering the data to be used by the workbook. Subject selection criteria may include, for example, age, weight, demographics, income, location, survey-based results, habits, markers, etc. Subject selection criteria may also allow the data for only one or more selected subjects to be used by the workbook.

The settings for a workbook may include notification settings, allowing the user to be notified via, for example, email, SMS, push notification delivery, IM, or otherwise when a reporting measure is available and/or a user-selected condition is met. For example, the user may configure the notifications to send a notification via e-mail when the marker metric shows an accuracy that drops below 90% or increases above 90%, if the marker is disabled/enabled, if the number of participants or events reaches a preferred limit.

The settings for a workbook may include logging/reporting URL options, which may provide the ability to generate updates that can be reviewed outside of the system (e.g., at a URL location). This option may be used, for example, for convenience or for secondary processing systems that can be utilized to further revise, compare, and share details to identified individuals.

The settings for a workbook may include dashboard settings, which provides the user with the ability to configure the workbook dashboard (e.g., FIG. 4).

The settings for a workbook may include settings for sharing a workbook, which may allow a user to grant and/or revoke various levels of read or write access to others. The settings for a workbook may include settings for authentication and API-related information for programmatically changing workbooks and configurations, as well as settings for creating callbacks and hooks into data reports and dashboards. The API-related interfaces may provide for alternate user-interface views and tools for users (e.g., providing settings relating to making manual or automatic changes when testing outcomes and collaborating across users).

At second row 602 of the interface are icons that correspond to the various modifications that can be done to the workbook's workflow. As shown in FIG. 6, second row 602 provides the options (from left to right) to edit the workbook, copy the workbook or elements of the workbook, add new inputs into the workbook, add new expressions to the workbook, add new result report parameters ("output") to the workbook, add text/notes to the workbook, and the ability to delete components of the workbook. Adding an input may provide the user with the option to specify the originating data source from the available data sources. Adding an expression may provide the user with the ability to quickly select from predefined template expressions or develop a custom expression. Adding a result report parameter may provide the user with the ability to identify information to include in the report for measuring success of the marker and for storing the results of the workbook. Storing the results of the workbook permits further analysis and even revision of the workbook (e.g., manually or through machine learning).

As shown in FIG. 6, expression 603 has been selected for editing, as provided in expression configuration 604. Expression configuration 604 may include fields (from top to bottom) for enablement of the expression, for entering a component name, for identifying an input measure, for identifying parameters for input (e.g., data) collection (such as when or how often the input is collected), for enablement of logging, and for selection of a coded expression 605, which may be a template coded expression (e.g., pre-defined "Expression 1"), a custom-coded new expression, or an edited template coded expression.

In some embodiments, the "enable" options may include on, off, or auto, where an auto expression may be controlled by another expression, allowing it to run in a dormant state while awaiting processing. Enabling the log may provide the user the ability to evaluate the behavior of the expression by reviewing the records in the log. In general, logging is advisable when observing the initial testing of a marker, but logging may be turned off when the marker is stabilized (e.g., the marker metric indicates that the marker score shows a stable and/or acceptable relationship with the outcome score) to reduce storage demands.

The input measure may be model based, where the component connected to the input of the module (e.g., device 102, input data storage 106) defines the available selections. For example, if a heart monitor is connected (e.g., if personal wearable device 102c is a heart monitor), the available input measures are subject to the database modeling available from the heart rate monitor, such as heart rate, heart rate variability, ECG, RR intervals. The available input measure for expression configuration 604 may also represent calculated values based on the input available from the heart monitor, such as peak value over a period of time. If an expression has multiple inputs, a list of available input measures for each connected input may be provided. This embodiment, however, is an ease-of-use measure for the user to make the system appeal to users with less knowledge in programming and model-based understanding. By restricting the user's choices to the available choices, human error may be reduced in configuring a workbook. But such a restriction of choices is optional, and this disclosure encompasses systems and methods that do not employ such restrictions.

The identification of parameters for the input (e.g., data) is shown as the "input collection/when" in expression configuration 604. This field may allow the user to specify, for example, how often the expression will be called to analyze the signal data source provided in the input measure. When live data is used, the selection of how often or when to collect the data can be used to turn on or off the data source (e.g., to turn on or off a sensor in personal device 102a or turn on or off personal device 102a entirely) when the data source is not required.

The coded expression 604 is modifiable to define a number of inputs, processing patterns, and enablements within the expression to adapt and evolve to the needs of the marker developed. Because the coded expression 604 can include algorithmic processing to help in defining ways to reduce false positives, the user can write her own code or pseudocode depending on the implementation, to manage the data and derivations of the data through the expression. This can provide a scientific workbook method to logging data and then analyzing data real-time and in a configurable redistributable mode of operation. The example shows the ability to initialize the code, and then through the main processing of the algorithm within the expression, how best to process the data and override the input measure before producing an output measure that can be tethered to another module. The custom code shown in coded expression 604, for example, may trigger the generation of forms that can be sent to a subject's device to request additional self-reporting measures that may help in revising the data collected and the false positives generated.

Figure 7A:
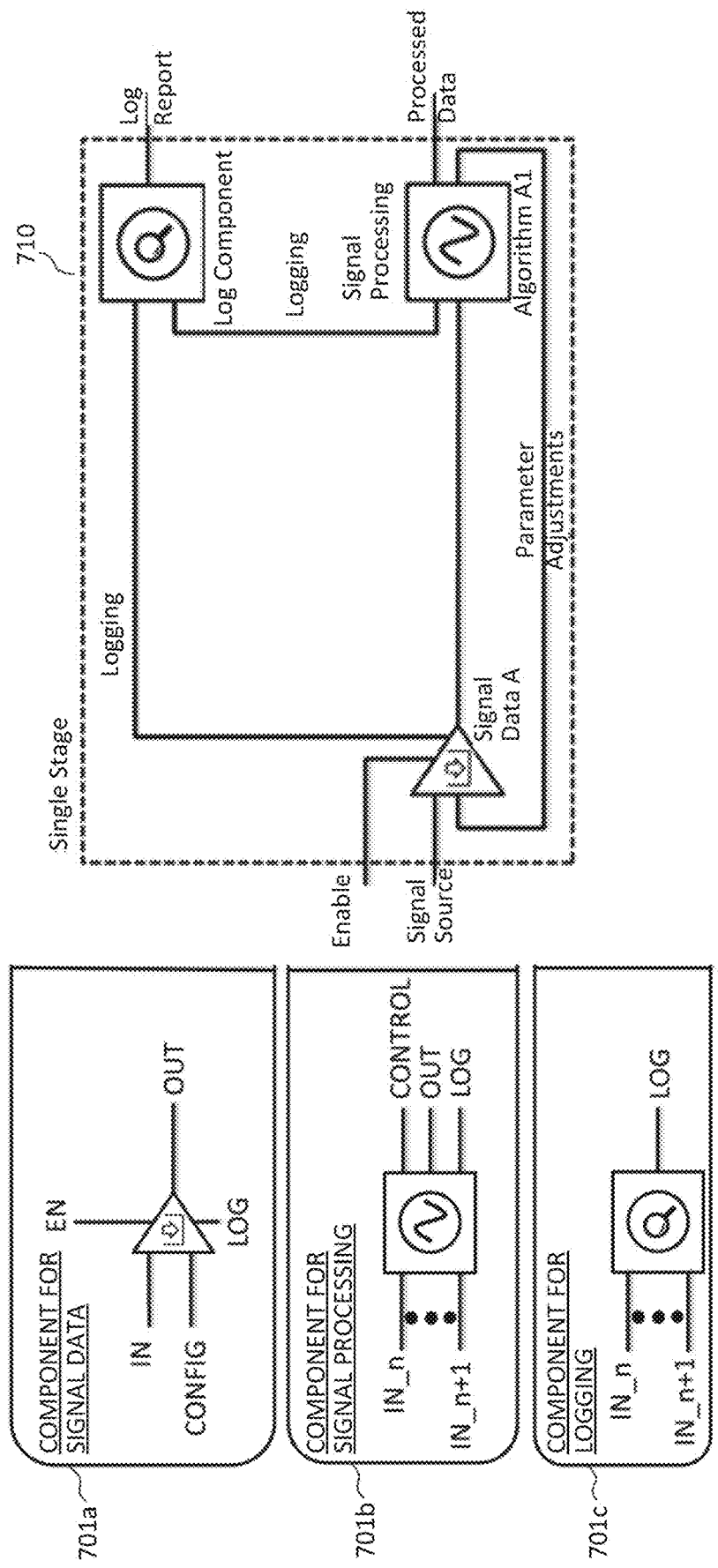
FIGS. 7a-d are diagrams of exemplary expression components (701 of FIG. 7a), which can be combined to provide exemplary pre-defined expressions (710, 720, 730, 740, 750 of FIGS. 7a-7c), which can be combined to provide an exemplary workbook project (shown in interface 700 of FIG. 7d).
Figure 7B:
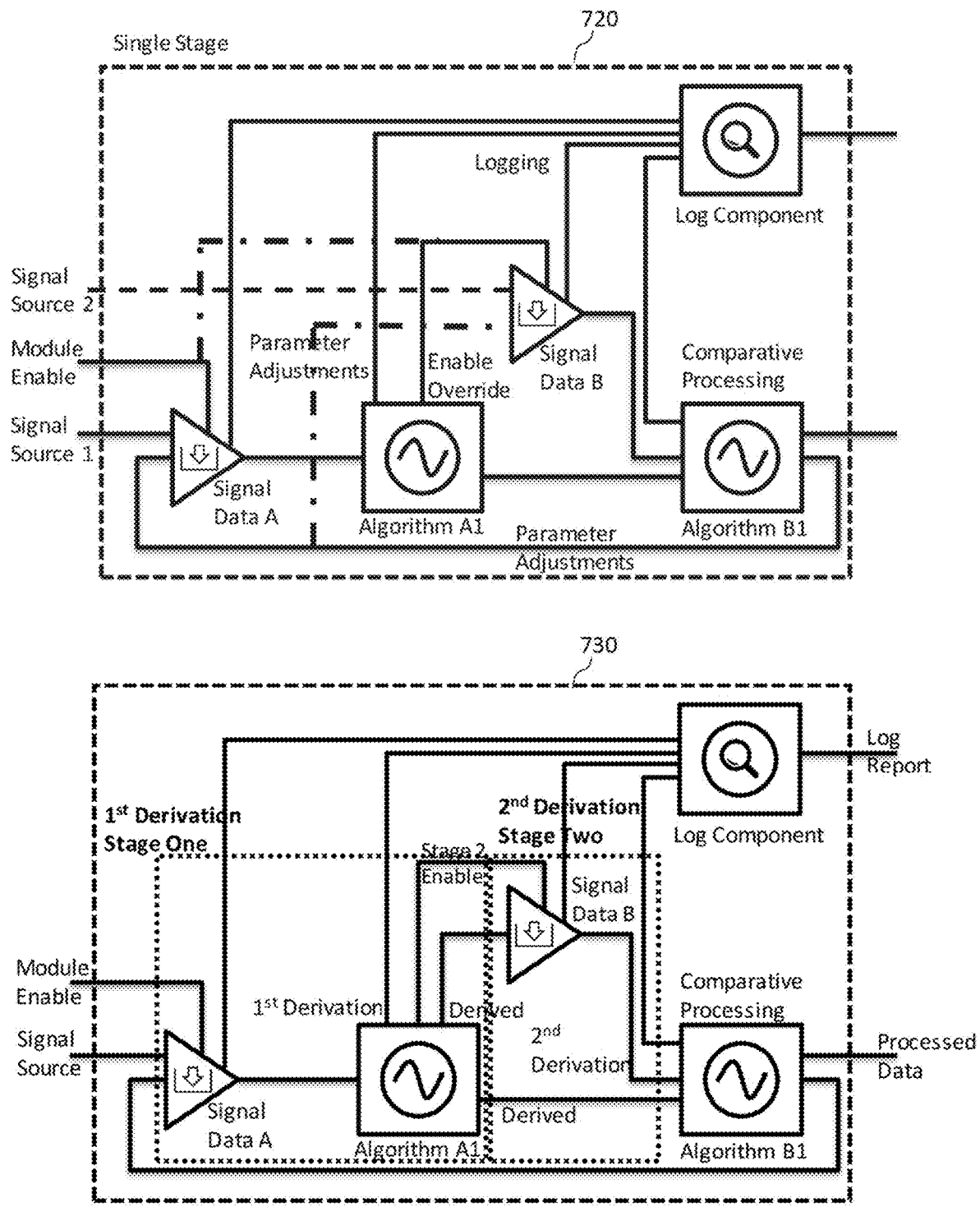
Figure 7C:
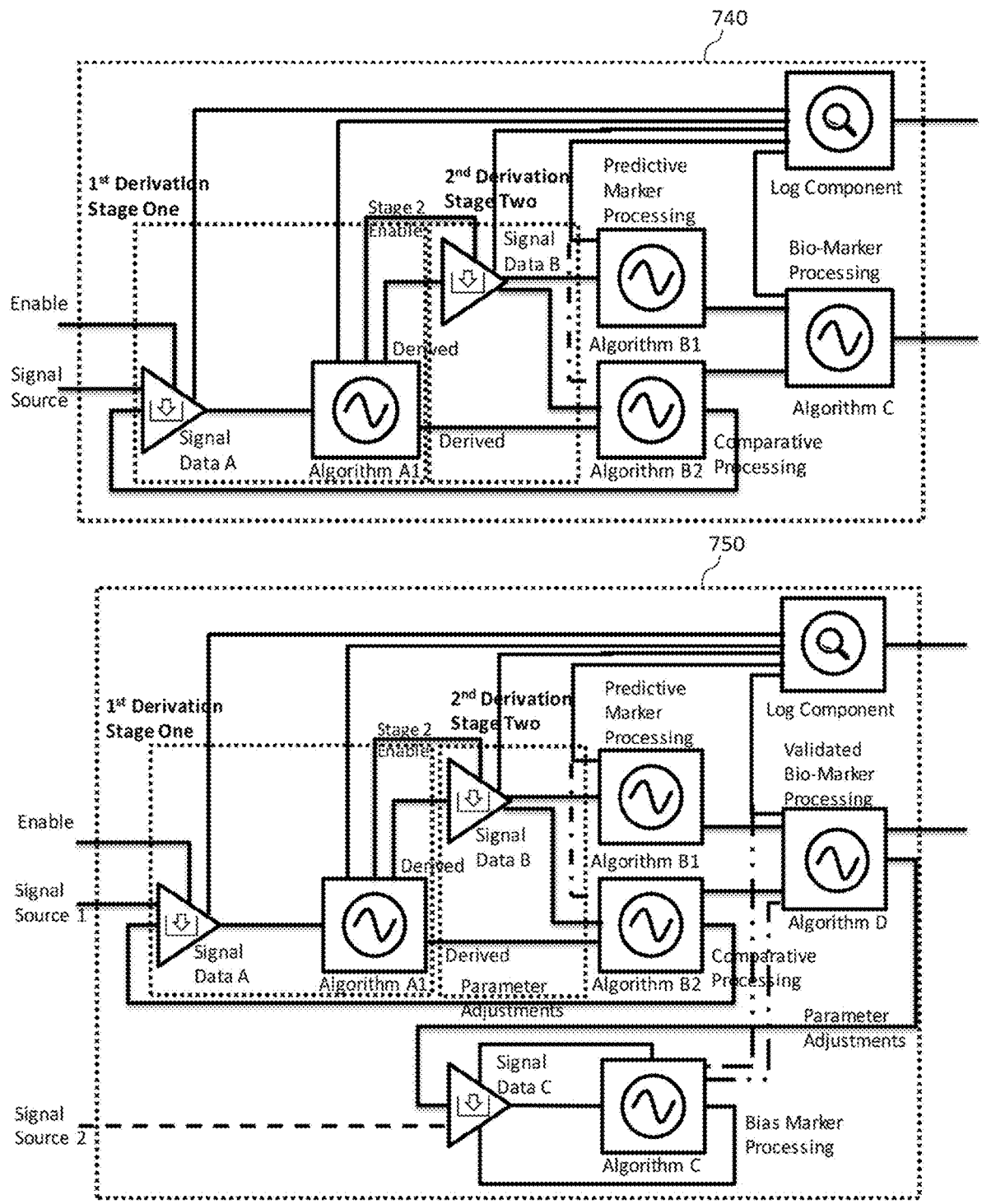
Figure 7D:
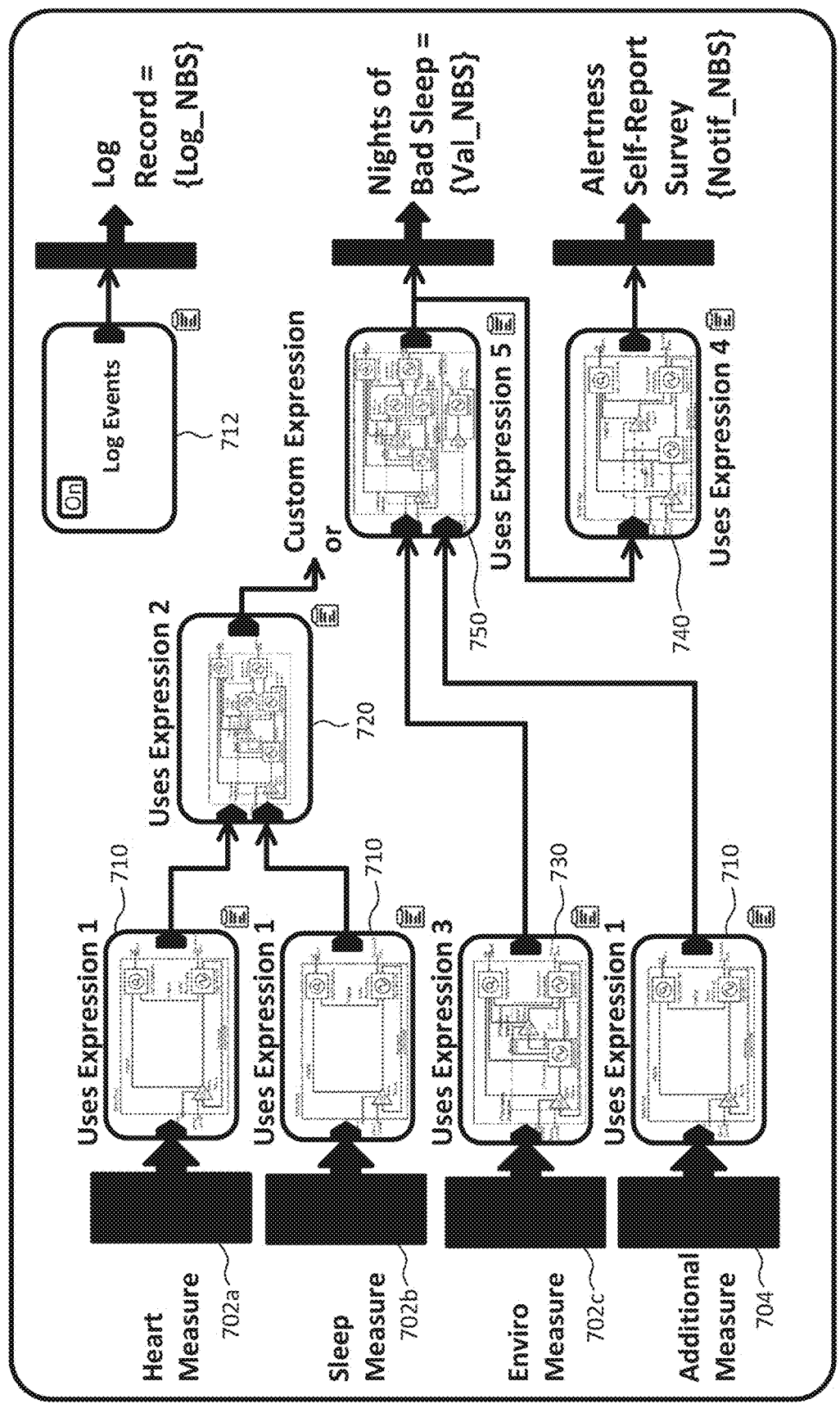

FIGS. 7a-7d provide diagrams of exemplary expression components (701 of FIG. 7a), which can be combined to provide exemplary pre-defined expressions (710, 720, 730, 740, 750 of FIGS. 7a-7c), which can be combined to provide an exemplary workbook project (shown in interface 700 of FIG. 7d). These figures demonstrate the system's ability to easily reconfigure expressions in a way that is transferrable to the community of users while adapting the exchange of observed data across the system based on changing needs through a workbook lab bench manager. Each of the following can be connected in any arrangement, any number of components or none as required for enabling custom expressions.

FIG. 7a provides diagrams for exemplary expression components 701a, 701b, and 701c and a diagram for pre-defined expression 710. Expression component 701a provides an exemplary diagram for a component for signal data. Expression component 701a enables availability of (IN) live momentary, streaming, or stored data source as a multivariable array or single variable array to be, for example, analyzed or collected (OUT) as needed, and with operations optionally logged (LOG). Customizations on the configuration (CONFIG) and enablement (EN) may also be provided. Expression component 701b provides an exemplary diagram for a component for signal processing. Expression component 701b component may enable multiple available data sources with modifiable instruction on the analysis across one to many data sources to create a processed output (OUT), with control signaling to other components (CONTROL), and optional logging (LOG). Expression component 701c provides an exemplary diagram for a component for logging. Expression component 701c enables aggregating multiple logs from components into a log handling routine that may be configured to self-manage component observations for the custom expression. Expression components 701 may be pre-configured components that a user may select for making an expression, or the user may create her own expression components 701.

Expression components 701 and/or other components may be combined to provide expressions. Expressions may be pre-defined expressions that a user may select when configuring a workbook, or the user may create her own expressions. An expression may provide the functionality of a predictor rule (when applied to data from a predictor variable class to generate a predictor score), of an outcome rule (when applied to data from an outcome variable class to generate an outcome score), or as an application of a marker relationship (when applied to a marker score and an outcome score to generate a marker metric).

For example, expression components 701a, 701b, and 701c have been combined to create the expression shown in FIG. 7a as expression 710. Expression 710 describes an expression that has a single input source 1, a defined enablement of the signal data Signal Data A, logging and modifiable parameters set by the algorithmic processing A1, also logged, which in turns generates the processed data output.

FIG. 7b provides further examples pre-defined expressions using expression components 701. Expression 720 can be considered a modification of expression 710. Expression 720 also combines a second signal input source 2 with a second algorithm B1 before providing the processed data output. The module enable can configure both signal sources as always on, always off or auto where the algorithm A1 of signal input source 1 can act as signal enable to the second signal input source 2. Expression 730 can be considered a modification of expressions 710 and 720. Expression 730 creates a second signal derivative of the single input source as Signal Data B derived from Signal Data A of the original single input signal and providing a two-stage operation with algorithms A1 and B1 before providing the processed data output.

FIG. 7c provides further examples expressions using expression components 701. Expression 740 can be considered a modification of expression 730. Expression 730 adds additional algorithm processing as Algorithm B2 and Algorithm C before providing the processed data output. Expression 750 can be considered a modification combining expressions 740 and 720. Expression 750 adds additional signal source 2 as signal data C and respective algorithm C with combined Algorithm D before providing the processed data output. Expression 750 also includes comparative processing, which is an example of a relationship rule. Thus, expression 750 functions as both a predictor rule and a marker relationship.

FIG. 7d is a diagram of an exemplary workbook interface 700, consistent with disclosed embodiments. This workbook is intended to test the model that heart data, sleep data, and environmental data (e.g., loud noises at night), can be used to determine a marker for a night of bad sleep by comparing the marker to some additional data that serves as the outcome data.

As shown in workbook interface 700, three predictor variable classes are selected: heart measure 702a, sleep measure 702b, and environmental measure 702c. Then one or more predictor rules (e.g., expressions) are applied to the data. For example, expression 710 is applied to the heart measure data and is separately applied to the sleep measure data, and the results of those two expressions are then combined using expression 720 to create a first predictor score (e.g., sleep duration is impacted by heart rate, for example, sleep quality as a predictor may be 7 of 10 when analyzing the two measures). Separately, expression 730 is applied to the environmental data to obtain a second predictor score (e.g., sound disruption is detected, and, based on prior data of the subject or her specific genomic data, it may suggest that some subjects are more affected by sound than others, thus, it may be weighted accordingly for each subject, providing, for example a predictor of 9 of 10 for a low-noise night when the subject is not likely impacted). An outcome rule, expression 710, is also applied to the additional measure data 704, to obtain an outcome score (e.g., alertness level throughout the day may be considered an outcome of sleep quality; for instance, when subject-reported entries indicate the previous night was bad or good, a trend of next day events tend to follow and may impact the subsequent night as well, and, in this case, an outcome of 3 of 10 may suggest that predictors have not captured a successful marker and can be flagged as inconclusive, or a 9 of 10 may suggest conclusive). Then, within expression 750, the predictor scores are combined with a marker rule to create a marker score, and the marker score is compared with the outcome score based on a marker relationship, and a marker metric is generated. The resulting output (e.g., "Nights of Bad Sleep={Val_NBS}) may include information about the marker metric to assist the user in determining whether the selected predictor variable classes can be used to detect a suitable marker for the desired outcome across a specific subject or class of subjects determined by, for example, bio-signatures or omics discoveries. This can then be modified further to introduce additional predictors that may be utilized to further refine for other individuals based on additional physiological (e.g., brain activity), behavioral (e.g., exercised before bed), or environmental (e.g. potential ambient light frequency disruptors) measures as needed to revise and improve the marker metrics.

A user may customize the expressions and the workbook. For example, a user may add or remove one or more of the predictor variable classes, change one or more of the expressions used, etc. In modifying the workbook, the data need not be re-collected as the stored data is available to re-run in the modified workbook. This is true even for adding predictor variable classes. Modifications may be performed by the user and/or automatically performed by the system (e.g., using machine learning) in order to determine a suitable and/or stable marker.

Figure 8:
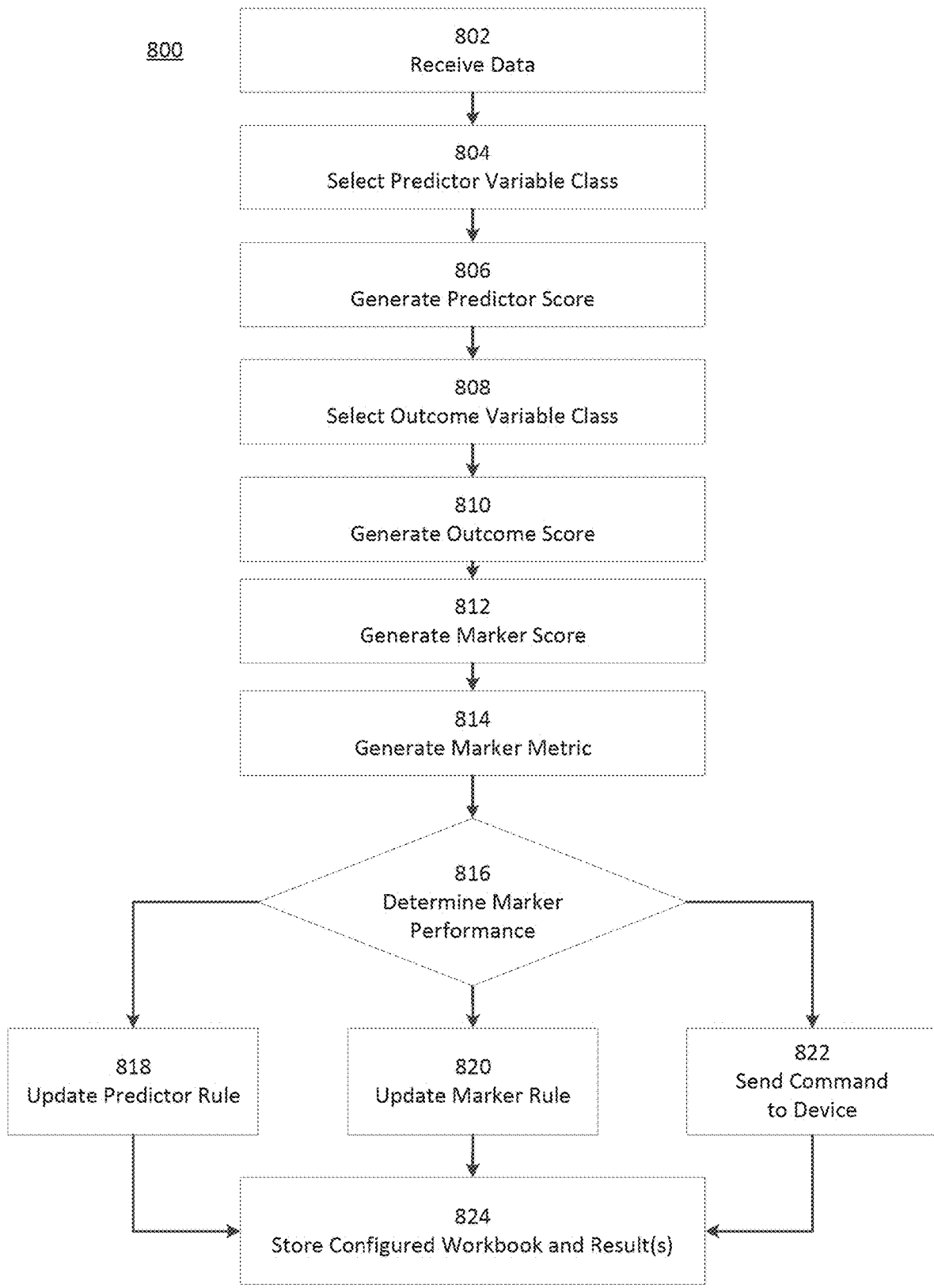
FIG. 8 is a diagram of an exemplary process for generating a marker, consistent with disclosed embodiments.

FIG. 8 is a diagram of an exemplary process 800 for generating a marker (e.g., identifying a marker using a workbook) performed by lab bench manager 116, consistent with disclosed embodiments. In some embodiments, process 800 may be performed to generate a marker based on one or more predictor variable classes and to determine performance of a marker. In some embodiments, process 800 may be performed as part of a workbook that is newly generated, generated based on a workbook template, and/or retrieved from configured bench storage 110.

At step 802, lab bench manager 116 receives data. Data may belong to one or more variable classes. In some embodiments, data of step 802 is received from input data storage 106. In some embodiments, data of step 802 is associated with a user. In some embodiments, data of step 802 may have one or more data collection parameters. In some embodiments, step 802 may include receiving one or more data collection parameters. In some embodiments, the received data is made accessible to a workbook.

At step 804, lab bench manager 116 selects one or more predictor variable classes (e.g., based on the configuration of the workbook). In some embodiments, a predictor variable class is selected based on data. In some embodiments, step 804 includes displaying a list of variable classes associated with received data and/or receiving inputs to identify a selected variable class (e.g., within the workbook interface environment). In some embodiments, a predictor variable class is selected according to a relationship between a predictor variable class and an outcome variable class. In some embodiments, step 804 involves a model (e.g., a machine-learning model).

At step 806, lab bench manager 116 generates one or more predictor scores (e.g., based on applying a predictor rule to the data according to the configuration of the workbook). In some embodiments, a predictor score is associated with a predictor variable class and is based on data and one or more predictor rules. In some embodiments, a predictor score may be, for example, a sleep-quality score, a duration of sleep score, a resting heart rate score, an enzyme level score, a hormone level score, a resting heart rate score, and/or an indicator of a presence or absence of a health condition score. In some embodiments, a predictor rule may include, for example, a data-processing technique, an algorithm, or a model (e.g., a machine learning model) (see, e.g., FIGS. 7a-d).

At step 808, lab bench manager 116 selects one or more outcome variable classes (e.g., based on the configuration of the workbook). In some embodiments, an outcome variable class is selected based on data. In some embodiments, step 808 includes displaying a list of variable classes associated with received data and/or receiving inputs to identify a selected variable class.

At step 810, lab bench manager 116 generates one or more outcome scores (e.g., based on applying an outcome rule to the data according to the configuration of the workbook). In some embodiments, an outcome score is associated with an outcome variable class and is based on data and one or more outcome rules. In some embodiments, an outcome score is, for example, a sleep-quality score, a duration of sleep score, a resting heart rate score, an enzyme level score, a hormone level score, a resting heart rate score, and/or an indicator of a presence or absence of a health condition score. In some embodiments, an outcome rule may include, for example, a data-processing technique, an algorithm, or a model (e.g., a machine learning model) (see, e.g., FIGS. 7a-d).

At step 812, lab bench manager 116 generates a marker score (e.g., according to the configured workbook). In some embodiments, a marker score is based on one or more predictor scores and one or more marker rules. In some embodiments, a marker score may be the same as a predictor score, a combination of predictor scores, and/or a transformed predictor score. In some embodiments, a marker rule may be applied to one or more predictor scores to generate a marker score. For example, lab bench manager 116 may (e.g., according to the configured workbook) combine a sleep score, a blood-pressure score, and a weight score to generate a marker score that reflects a state of health (e.g., a level of stress).

At step 814, lab bench manager 116 generates a marker metric. In some embodiments, a marker metric is based on one or more marker scores, one or more outcome scores, and one or more marker relationships.

At step 816, lab bench manager 116 determines a marker performance. In some embodiments, a marker performance is based on a marker metric. In some embodiments, step 816 includes determining whether a marker metric satisfies a performance criterion such as a threshold value or comparing the determined marker metric value to a previously determined marker metric value. In some embodiments, an action is performed (e.g., a command to update a data collection parameter, to update a predictor rule, to update marker rule, to update an outcome rule) if the marker satisfies a performance criterion. In some embodiments, an action is performed is if the marker does not satisfy a performance criterion. In some embodiments, an action is not performed if the marker satisfies a performance criterion. In some embodiments, and action is not performed if the marker does not satisfy a performance criterion. In some embodiments, different actions may be performed or not performed depending on the level of satisfaction of the criterion by the marker.

At step 818, lab bench manager 116 updates a predictor rule (e.g., updates the expression used in the workbook to determine the predictor score). In some embodiments, a predictor rule is updated based on a marker metric. In some embodiments, a predictor rule is updated to improve a marker metric.

At step 820, lab bench manager 116 updates a marker rule (e.g., updates the expression used in the workbook to determine the marker score). In some embodiments, a marker rule is updated to improve a marker metric.

At step 822, lab bench manager 116 may send a command to a device (e.g., a device 102). In some embodiments, a device is associated with a user and data (e.g., personal device 102a). In some embodiments, a command is sent to update one or more data collection parameters and/or the type of data collected. For example, a command may be to change a rate of data collection, a type of data collection, and/or a device setting. In some embodiments, a command is sent to a device capable of performing an operation (e.g., administration device 102e), and the command causes the device to perform an operation.

At step 824, lab bench manager 116 stores a workbook that reflects the marker analysis and the results and data associated with the workbook. In some embodiments, a workbook is stored in memory such as configured bench storage 110. In some embodiments, a result is stored in memory such as processed data storage 112. In some embodiments, a result is a predictor score, an outcome scores, a marker score, and/or a marker metric. In some embodiments, a workbook includes one or more predictor rules, one or more outcome rules, and one or more marker relationships.

Figure 9:
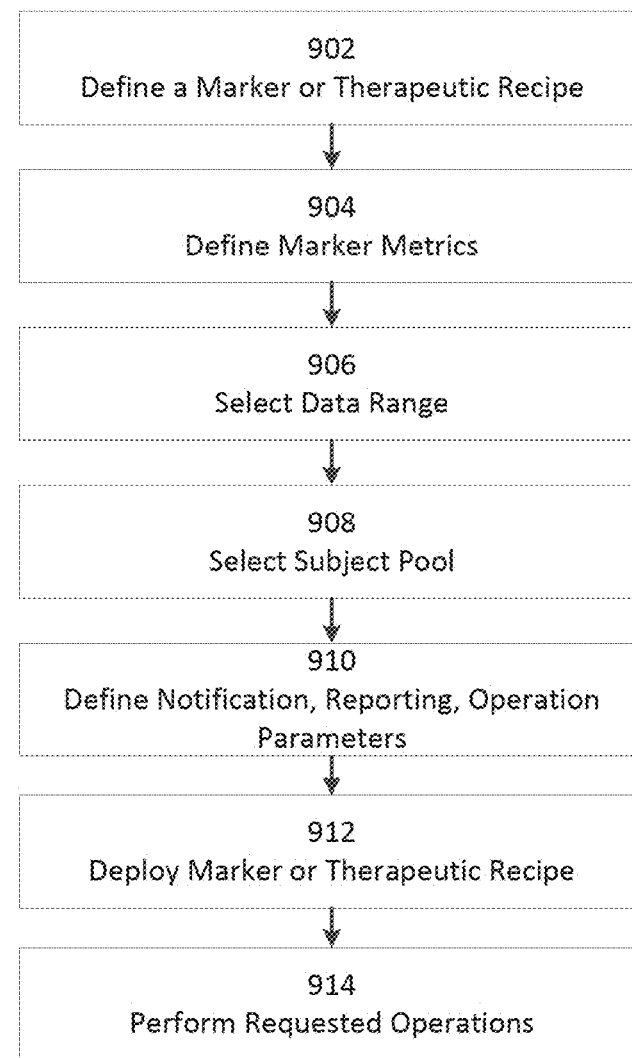
FIG. 9 is a diagram of an exemplary process for providing a therapeutic recipe, consistent with disclosed embodiments.

FIG. 9 is a diagram of an exemplary process 900 for providing a therapeutic recipe, consistent with disclosed embodiments. Generating a therapeutic recipe is similar to generating a marker. A therapeutic recipe, however, is often intended to identify and/or monitor a therapeutic for an individual subject, e.g., using the information about a subject's particular marker scores to recommend and/or perform therapeutic actions.

At step 902, lab bench manager 116 receives a definition of a marker or a therapeutic recipe. The definition of a marker or therapeutic recipe is often based on a stable marker and/or a marker with a marker metric that is acceptable to the user and/or subject. For example, if the workbook developed in FIG. 5 shows that the sleep, blood pressure, and weight predict medication adherence, then the same sleep, blood pressure, and weight variable classes (e.g., predictor variable classes 502a-502c) and the same expressions (e.g., expressions 506a-506c and 510) may be used to define the marker or therapeutic recipe at step 902.

At step 904, marker metrics are defined. Marker metrics specify the intended outcome percentile of acceptance, error tolerances, and process capability statistics. This provides the ability to define notifications when acceptable ranges are met or not met and adjustments should be considered and revisited to the marker design.

At step 906, a data range is selected. A data range setting may, for example, describe a start date of today with a specific end date or no end date (e.g., indicating the collection of live data), a specific pre-existing range (e.g., indicating the use of stored data), a range of unique data points (may not be attributed to a date or time depending on the data source), or a combination of these options. The system may be configured to indicate if data is unavailable on a given date. For therapeutic recipes that are intended for ongoing monitoring a subject, a data range indicating the collection of live data may be specified.

At step 908, the subject pool is selected. The subject pool may be selected based on criteria such as age, weight, demographics, income, location, survey-based results, etc. Subject selection criteria may also allow the data for only one or more selected subjects (e.g., the subjects for whom the therapeutic recipe is being developed).

At step 910, the notification, reporting, and operation parameters are defined. This is where the user identifies the actions the system is to take depending on the data obtained and the model. For example, the user may configure the system to send an e-mail notification when data indicating the subject is not complying with recommendations or within the performance metrics associated with the model, to automatically update the model based on the data, or to send a command to an administration device 102e based on the model and/or data.

At step 912, the marker or therapeutic recipe is deployed, i.e., the model is allowed to run, collecting and analyzing data and providing notifications, reporting, and operations according to the definitions provided in steps 902-910.

At step 914, the user and/or subject may request further operations be performed by the system while the model is running. For example, a user may share the marker or therapeutic recipe workbook with another user, a user may modify the model (or a system using machine learning may be programmed to modify the model automatically), a user may request further information and/or notifications on risks and/or responses detected while the model is running, a subject may request information about the model and/or her own data.

Figure 10:
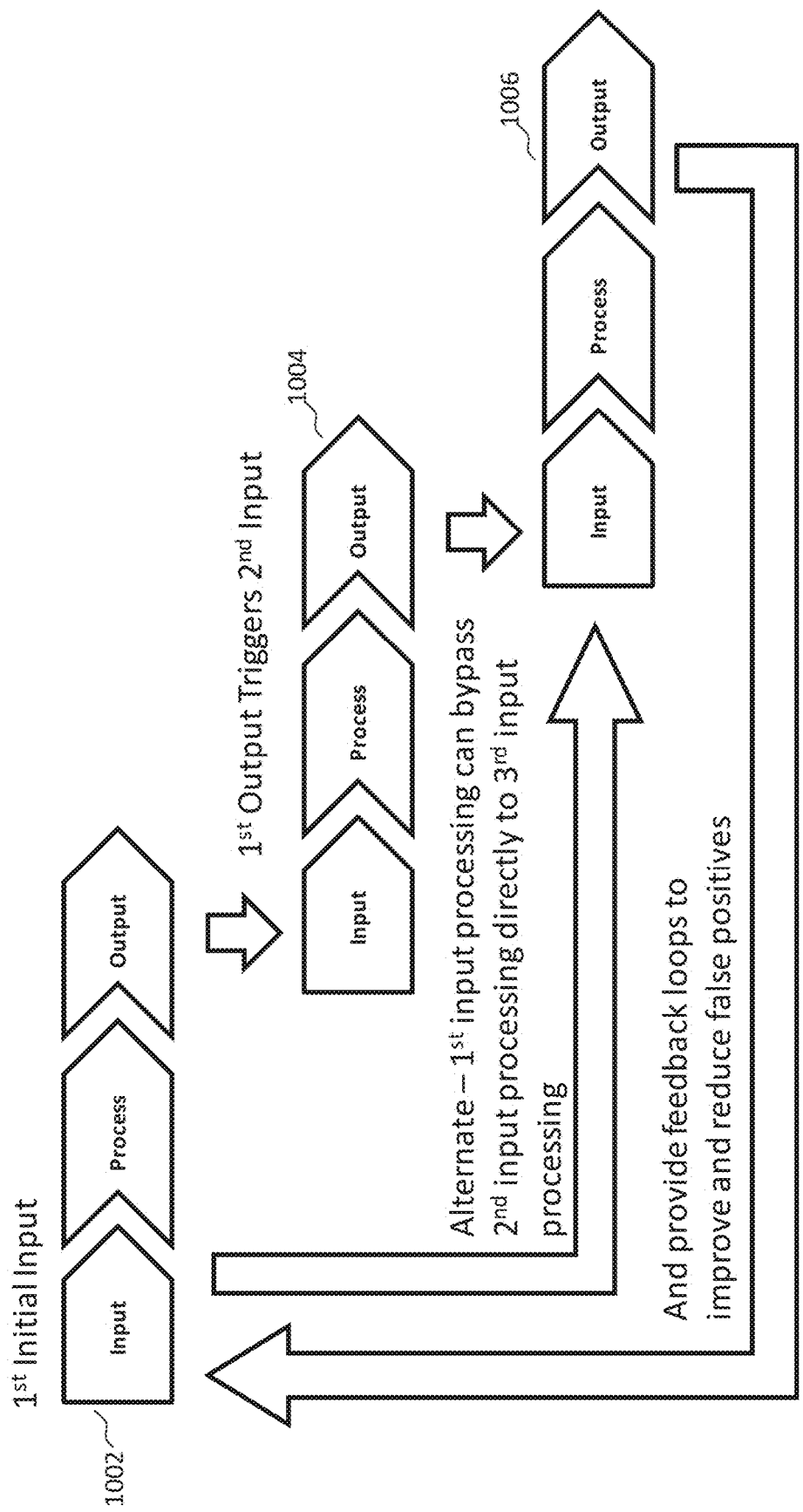
FIG. 10 is a conceptual diagram of an exemplary benefit of disclosed systems and methods.

FIG. 10 provides a conceptual diagram of an exemplary benefit of the disclosed systems and methods.

Models for identifying markers can be considered, at a high level, as comprising the operations of comprising input to produce output, with the output data then being used as input for the next step of the model. This is demonstrated by the flow of information from the first initial input at step 1002, which is processed to produce output that is used as the second input for step 1004, which is processed to produce output that is used as the third input for step 1006, and so on.

Because of the inflexibility of current systems, changing the data flow programmatically may be difficult, if not impossible. But changing the data flow is desirable because it can reduce the data being recorded, transmitted, stored, and processed; reduce costs, reduce inconveniences for the user and/or the subject; increase collaboration between users and/or users and subjects; and generally lead to a better understanding of the markers of an outcome.

The disclosed systems and methods allow for identification of processes that may be bypassed with minimal to no effect on the results. For example, a user may initially develop the three-step model represented by steps 1002, 1004, and 1006 using lab bench manager 116, but the user may manually remove and/or bypass expression 1004 to see if the results are still acceptable using only a two-step system (see the "Alternate" arrow of FIG. 10). In some embodiments, machine learning may be used to test various configurations of inputs and expressions to develop an effective model (e.g., a model that meets a pre-defined criteria). In some embodiments, the parameters of the data used as input may be changed. In some embodiments, the output of the model (e.g., the output of step 1006) may be used as the initial input to create a feedback loop to even further improve the model and/or reduce false positives.

For example, a model may be created to test the hypothesis that a heart measure, sleep measure, and environmental measure create a marker for a bad night of sleep, wherein the input for the environmental measure includes monitoring the bedroom for noise (e.g., under a hypothesis that a noisy environment makes it difficult to sleep). But through manipulation of the model using lab bench manager 116 (either manually or using machine learning), it may be found that noise monitoring throughout the day does not affect the results, so data collection can be reduced, for example, to monitoring only at night or only when another sensor detects the subject to be in the bedroom. Or it may even be found that noise levels have minimal or no effect on determining a bad night of sleep, so that expression may be eliminated altogether.

Reduction of data collection may reduce processing needs of the device, improve battery life, reduce bandwidth consumption between the sensor and the input network, reduce the amount of data managed and stored in the input data storage and reduce further exchanges and processing by cloud based server or serverless deployment designs in the simultaneous management of stream data and extremely large storage systems with the exchange and processing demand of such systems.

A benefit of the disclosed system is that it not only allows users to identify makers, but it also allows subjects to benefit from the data obtained and analyses conducted by the system. Once a marker is developed, e.g., a marker with a marker metric that is stable and/or indicates a level of confidence or predictability for an outcome that is acceptable to the user and/or subject, the information garnered from the model can be used in a variety of ways. As disclosed herein, information collected and/or generated using the disclosed methods and systems can be used by the system to, for example, send or transmit a notification to a user and/or subject. For example, the system may transmit a notification to a user about the functioning of the model, potential improvements to the model, data about one or more subjects. The system may transmit a notification to a subject (e.g., via an interface of personal device 102a) that she is meeting goals related to the marker or suggestions for affecting a predicted outcome. The system may also send or transmit a notification to a contact associated with the subject. For example, the system may transmit a notification comprising a subject's data to the subject's health care provider or a notification with a suggestion to a contact associated with the subject (e.g., a notice to a friend suggesting that the friend call the subject if the subject is showing markers for depression). These notifications may be transmitted, for example, based on a request by the user, subject, and/or contact, triggered by the data collected about a subject or subjects, periodically based on a schedule, or triggered by a change in the model.

Information collected and/or generated using the disclosed methods and systems can then be used by the system to, for example, transmit a command to a device (e.g., administration device 102e) to perform an operation for and/or to the subject. For example, operations may include administration of a drug to the subject by a device connected to the system, changing of a dose or dosing schedule of a drug administered by a device connected to the system, adjusting and/or turning on or off a device that affects the environment of the subject (e.g., reducing the temperature at night by a thermostat connected to the system based on a marker indicating that lower temperatures improve sleep quality and data received by the thermostat that the temperature is above optimal).

Another benefit of the disclosed system is that it allows for continuous optimizing of markers and adjustments based on new data. As disclosed herein, information collected and/or generated using the disclosed methods and systems can be used to update a rule, a data collection parameter, an output, and/or a relationship.

These operations may also be performed while the model is being developed, e.g., to assist in optimizing the inputs, expressions, and relationships of the model. For example, the system may send a command to a device 102 to alter data collection parameters and/or turn a device on or off in order to obtain the data needed for an updated model, or the system may send a notification to a subject with a suggestion for the subject to change her activities in a way that will provide the model with the information needed to test an update to a model.

Given the flexibility and potential for constant optimization of the model, the line between research to identify a marker and implementation of the results into therapeutic recipes may essentially blur.

The lab bench manager (e.g., the workbook projects of the lab bench manager) may also be used to determine when subjects are providing inaccurate information (e.g., lying, forgetting, making a mistake). For example, when a subject provides self-reported information that is inconsistent with a model, this may be an indicator that the information provided is inaccurate.

The foregoing description has been presented for purposes of illustration. It is not exhaustive and is not limited to precise forms or embodiments disclosed. Modifications and adaptations of the embodiments will be apparent from a consideration of the specification and practice of the disclosed embodiments. For example, while certain components have been described as being connected to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from a consideration of the specification and practice of the embodiments disclosed herein. It is intended that the specification and examples be considered as an example only, with a true scope and spirit of the disclosed embodiments being indicated by the following claims.

What is claimed is:

1. An interactive system for generating a marker for a health outcome based on physiological or behavioral data, the system comprising:
   a network interface providing communication with one or more devices over a communication network;
   a database storing sensor data and subject-reported data collected from remote devices over the communication network; and
   a server system comprising one or more computers and one or more computer-readable media that store instructions that are operable, when executed by the one or more computers, to cause the one or more computers to perform operations comprising:
      providing, to a user device over the communication network, an interface to specify and adjust relationships among data sources and data processing operations in a marker for a health outcome;
      identifying, based on data in the database, a set of available variable classes for which (i) stored data is available in the database or (ii) data can be obtained from remote devices, the set of available variable classes including measurements for at least one of physiological or behavioral parameters;
      providing, to the user device, an indication of the available variable classes to the user device;
      receiving, from the user device, data indicating a selection of a subset of the available variable classes;
      generating a marker definition for a marker for a health outcome based on the selected subset of variable classes, the marker being configured to generate a marker score indicative of the health outcome based on input values for the variable classes in the selected subset;
      applying the marker specified by the marker definition to a data set, including (i) generating marker scores for examples in the data set using the marker and (ii) evaluating performance of the marker including accuracy of the marker scores in predicting the health outcome, wherein evaluating the performance of the marker comprises determining whether a measure of the performance of the marker satisfies at least one performance criterion; and
      based on determining that the measure of the performance of the marker satisfies the at least one performance criterion, enabling one or more devices to apply the marker, including causing a remote device to perform data collection for the subset of variable classes used in the marker such that a marker score for the marker is generated based on data collected by the remote device.

2. The system of claim 1, wherein the operations comprise:
   generating a measure of accuracy of the marker;
   determining that the measure of accuracy satisfies a threshold; and
   issuing a notification in response to determining that the measure of accuracy satisfies the threshold.

3. The system of claim 1, wherein applying the marker to the data set indicated by the user device comprises applying the marker to stored dataset that is stored in the database.

4. The system of claim 1, wherein applying the marker to the data set indicated by the user device comprises applying the marker to an incoming data stream provided by at least one remote device.

5. The system of claim 1, wherein enabling the one or more devices to apply the marker comprises causing the one or more devices to perform data collection for the variable classes indicated in the marker definition and apply the marker to the data collected by the one or more remote devices.

6. The system of claim 1, wherein enabling the one or more devices to apply the marker comprises (i) causing each of multiple remote devices to perform data collection for the subset of variable classes used in the marker and (ii) causing a marker score for the marker to be generated for each of the remote devices, wherein the marker score generated for each remote device is based on the data collected by the remote device.

7. The system of claim 1, wherein the marker definition is based on user interaction with a user interface that includes interactive elements providing visual representations of processing operations that are components used to generate a value for the marker, the interactive elements being movable in the user interface to change the operation of the marker.

8. The system of claim 1, wherein the operations comprise:
providing user interface data for presentation in a user interface of the user device, the user interface comprising a user-reconfigurable arrangement of visual elements that represent relationships among data sources and data processing operations for developing the marker; and
receiving user input data from the user device indicating user manipulation of the visual elements that represent the data sources and data processing operations in the user interface; and
wherein the marker definition is generated to include a set of data processing operations determined based on an arrangement of the visual elements set by the user manipulation of the visual elements in the user interface.

9. The system of claim 1, wherein the marker is a marker for one or more effects of a medication.

10. The system of claim 1, wherein the marker is a marker indicating a level of impact of a therapy for an individual.

11. The system of claim 1, wherein the marker is a marker that indicates a health risk for an individual.

12. The system of claim 1, wherein the operations comprise:
including the marker definition in a repository of shared markers provided to multiple users; and
selectively enabling access to the marker to one or more of the multiple users.

13. A method performed by one or more computers, the method comprising:
providing, to a user device over the communication network, an interface to specify and adjust relationships among data sources and data processing operations in a marker for a health outcome;
identifying, based on data in the database, a set of available variable classes for which stored data is available in the database or (ii) data can be obtained from remote devices, the set of available variable classes including measurements for at least one of physiological or behavioral parameters;
providing, to the user device, an indication of the available variable classes to the user device;
receiving, from the user device, data indicating a selection of a subset of the available variable classes;
generating a marker definition fora marker fora health outcome based on the selected subset of variable classes, the marker being configured to generate a marker score indicative of the health outcome based on input values for the variable classes in the selected subset;
applying the marker specified by the marker definition to a data set, including (i) generating marker scores for examples in the data set using the marker and (ii) evaluating performance of the marker including accuracy of the marker scores in predicting the health outcome, wherein evaluating the performance of the marker comprises determining whether a measure of the performance of the marker satisfies at least one performance criterion; and
based on determining that the measure of the performance of the marker satisfies the at least one performance criterion, enabling one or more devices to apply the marker, including causing a remote device to perform data collection for the subset of variable classes used in the marker such that a marker score for the marker is generated based on data collected by the remote device.

14. The method of claim 13, comprising:
generating a measure of accuracy of the marker;
determining that the measure of accuracy satisfies a threshold; and
issuing a notification in response to determining that the measure of accuracy satisfies the threshold.

15. The method of claim 13, wherein applying the marker to the data set indicated by the user device comprises applying the marker to stored dataset that is stored in the database.

16. The method of claim 13, wherein applying the marker to the data set indicated by the user device comprises applying the marker to an incoming data stream provided by at least one remote device.

17. The method of claim 13, wherein enabling the one or more devices to apply the marker comprises causing the one or more devices to perform data collection for the variable classes indicated in the marker definition and apply the marker to the data collected by the one or more remote devices.

18. The method of claim 13, wherein enabling the one or more devices to apply the marker comprises (i) causing each of multiple remote devices to perform data collection for the subset of variable classes used in the marker and (ii) causing a marker score for the marker to be generated for each of the remote devices, wherein the marker score generated for each remote device is based on the data collected by the remote device.

19. The method of claim 13, wherein the marker definition is based on user interaction with a user interface that includes interactive elements providing visual representations of processing operations that are components used to generate a value for the marker, the interactive elements being movable in the user interface to change the operation of the marker.

20. One or more non-transitory computer-readable media that store instructions that are operable, when executed by one or more computers, to cause the one or more computers to perform operations comprising:
providing, to a user device over the communication network, an interface to specify and adjust relationships among data sources and data processing operations in a marker for a health outcome;

identifying, based on data in the database, a set of available variable classes for which (i) stored data is available in the database or (ii) data can be obtained from remote devices, the set of available variable classes including measurements for at least one of physiological or behavioral parameters;

providing, to the user device, an indication of the available variable classes to the user device;

receiving, from the user device, data indicating a selection of a subset of the available variable classes;

generating a marker definition fora marker fora health outcome based on the selected subset of variable classes, the marker being configured to generate a marker score indicative of the health outcome based on input values for the variable classes in the selected subset;

applying the marker specified by the marker definition to a data set, including (i) generating marker scores for examples in the data set using the marker and (ii) evaluating performance of the marker including accuracy of the marker scores in predicting the health outcome, wherein evaluating the performance of the marker comprises determining whether a measure of the performance of the marker satisfies at least one performance criterion; and based on determining that the measure of the performance of the marker satisfies the at least one performance criterion, enabling one or more devices to apply the marker, including causing a remote device to perform data collection for the subset of variable classes used in the marker such that a marker score for the marker is generated based on data collected by the remote device.

* * * * *